(12) United States Patent
Smet et al.

(10) Patent No.: US 12,740,901 B2
(45) **Date of Patent: *Sep. 22, 2026**

(54) ABSORBENT ARTICLE WITH IMPROVED BOTTOM DISTRIBUTION ASSEMBLY

(71) Applicant: Drylock Technologies NV, Zele (BE)

(72) Inventors: Steven Smet, Zele (BE); Tom Derycke, Zele (BE); Werner Van Ingelgem, Zele (BE); Bart Van Malderen, Zele (BE)

(73) Assignee: Drylock Technologies NV, Zele (BE)

( * ) Notice: Subject to any disclaimer, the term of this patent is extended or adjusted under 35 U.S.C. 154(b) by 409 days.

This patent is subject to a terminal disclaimer.

(21) Appl. No.: 18/257,337

(22) PCT Filed: Nov. 25, 2021

(86) PCT No.: PCT/EP2021/083004
§ 371 (c)(1),
(2) Date: Jun. 14, 2023

(87) PCT Pub. No.: WO2022/128391
PCT Pub. Date: Jun. 23, 2022

(65) Prior Publication Data

US 2024/0024174 A1 Jan. 25, 2024

(30) Foreign Application Priority Data

Dec. 18, 2020 (NL) .................................... 2027163

(51) Int. Cl.
*A61F 13/537* (2006.01)
*A61F 13/15* (2006.01)
(Continued)

(52) U.S. Cl.
CPC .. *A61F 13/53756* (2013.01); *A61F 13/15203* (2013.01); *A61F 13/4756* (2013.01);
(Continued)

(58) Field of Classification Search
CPC ............. A61F 13/53756; A61F 13/531; A61F 2013/5315; A61F 13/534;
(Continued)

(56) References Cited

U.S. PATENT DOCUMENTS 6,491,777 B1 12/2002 Bevins, III et al.
6,835,192 B1 * 12/2004 Guidotti ........... A61F 13/53708 604/385.101

(Continued)

FOREIGN PATENT DOCUMENTS

EP 0749736 12/1996
EP 0924328 6/1999

(Continued)

OTHER PUBLICATIONS

"International Application Serial No. PCT/EP2021/083004, International Search Report dated Jan. 17, 2022", (Jan. 17, 2022), 3 pgs.

(Continued)

*Primary Examiner* — Jacqueline F Stephens
*Assistant Examiner* — Arjuna P Chatrathi
(74) *Attorney, Agent, or Firm* — Schwegman Lundberg & Woessner, P.A.

(57) ABSTRACT

An absorbent article comprising a liquid pervious topsheet (300), a liquid impervious backsheet (200), absorbent material positioned between the liquid pervious topsheet and the liquid impervious backsheet, and a bottom distribution assembly between the absorbent material and the liquid impervious backsheet, wherein the absorbent material comprises superabsorbent particles and is arranged such that one or more channels are formed, wherein substantially no absorbent material is present in the one or more channels, wherein the bottom distribution assembly comprises a first layer and a second layer, wherein said first layer has a first density between 20 and 150 kg/m3 and said second layer has (Continued)

a second density between 100 and 400 kg/m3, said second density being higher than the first density, wherein said first layer is closer to the absorbent material than said second layer.

24 Claims, 9 Drawing Sheets

(51) Int. Cl.
*A61F 13/475* (2006.01)
*A61F 13/534* (2006.01)

(52) U.S. Cl.
CPC .................. *A61F 13/53717* (2013.01); *A61F 2013/15406* (2013.01); *A61F 2013/15422* (2013.01); *A61F 2013/5349* (2013.01); *A61F 2013/53721* (2013.01)

(58) Field of Classification Search
CPC .......... A61F 2013/5349; A61F 13/5323; A61F 13/532; A61F 13/53743; A61F 13/537; A61F 13/15577; A61F 13/4756; A61F 13/53717
See application file for complete search history.

(56) References Cited

U.S. PATENT DOCUMENTS

| | | | |
|---|---|---|---|
| 8,268,424 B1 | 9/2012 | Suzuki et al. | |
| 2004/0077247 A1 | 4/2004 | Schmidt et al. | |
| 2005/0027267 A1 | 2/2005 | Van et al. | |
| 2006/0025733 A1 | 2/2006 | Kikuchi et al. | |
| 2011/0217894 A1* | 9/2011 | Coslett | D04H 3/14 442/382 |
| 2015/0065973 A1* | 3/2015 | Roe | A61F 13/533 604/374 |
| 2015/0080821 A1 | 3/2015 | Peri et al. | |
| 2016/0175169 A1* | 6/2016 | Bianchi | A61F 13/15658 604/385.101 |
| 2018/0353353 A1* | 12/2018 | Konawa | A61F 13/532 |
| 2019/0136426 A1 | 5/2019 | Hansen et al. | |
| 2019/0345655 A1* | 11/2019 | Chester | B32B 5/26 |
| 2019/0351648 A1* | 11/2019 | Parsons, IV | B32B 5/022 |
| 2020/0016013 A1* | 1/2020 | Mecl | B32B 5/022 |
| 2020/0392658 A1* | 12/2020 | Ren | D06N 3/0038 |

FOREIGN PATENT DOCUMENTS

| | | | |
|---|---|---|---|
| EP | 0951593 | 2/2002 | |
| EP | 1520687 | 4/2005 | |
| EP | 2437703 | 9/2013 | |
| EP | 2946755 | 11/2015 | |
| EP | 3167858 | 5/2017 | |
| EP | 3388039 A1 | 10/2018 | |
| EP | 3403631 A1 | 11/2018 | |
| EP | 3466388 | 4/2019 | |
| EP | 3403630 B1 * | 8/2019 | A61F 13/4756 |
| EP | 3403632 B1 | 8/2019 | |
| EP | 3560469 A1 | 10/2019 | |
| EP | 3603592 | 2/2020 | |
| EP | 3711732 | 9/2020 | |
| WO | 2012170778 | 12/2012 | |
| WO | 2014093128 | 6/2014 | |
| WO | 2015031243 | 3/2015 | |
| WO | WO-2015031229 A1 | 3/2015 | |
| WO | 2015066300 | 5/2015 | |
| WO | 2019158226 | 8/2019 | |

OTHER PUBLICATIONS

"International Application Serial No. PCT/EP2021/083004, Written Opinion dated Jan. 17, 2022", (Jan. 17, 2022), 7 pgs.
Das, Dipayan, "Composite Nonwoven Materials", Woodhead section 1.2.3, 2014, 5 pages.
Edana, Nonwovens Standard Procedure, "Nonwoven Thickness", Reference No. NWSP 120.6.RO 15, 2011, 11 pages.
Edana, Nonwovens Standard Procedures, "Mass per Unit Area", Reference No. NWSP 130.1.R0 20, 2010, 6 pages.
Ghent University, "SMS Technical Report", Report No. 23-0307-01, Jul. 15, 2025, 8 pages.
Microgard, "1500 Fabric SMS Technical Data Sheet", Woodhead Publishing Series in Textiles No. 155, 2011, 7 pages.

* cited by examiner 300
600
110
100
700
120
200
160
170
130

400
300
110
100
800
200
130

300
400
100
400
130
200
800

801
800
802

300
130
130
400,110
800
200
160
170
801
802

100
170
140
600
130
110,120
160
150

100
160
140
130
110,800
170
150
400

800
160
140
130
100
170
150
400

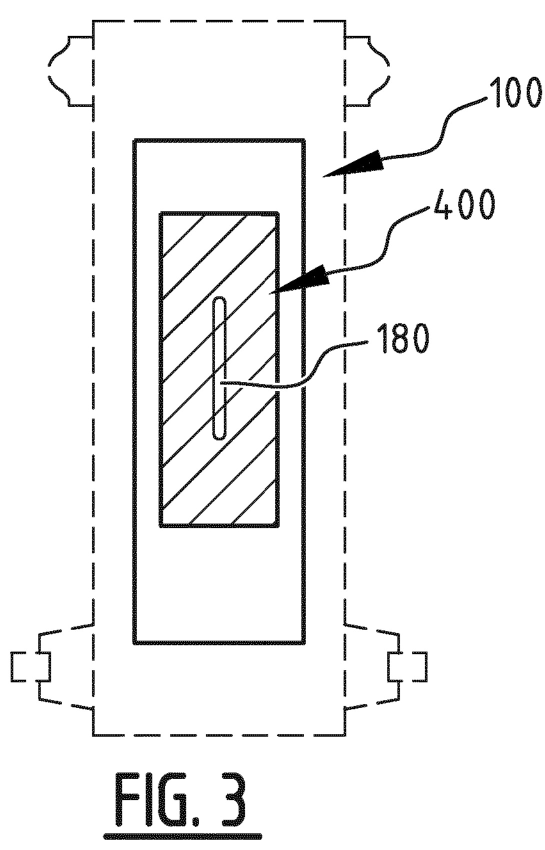
FIG. 3
FIG. 4
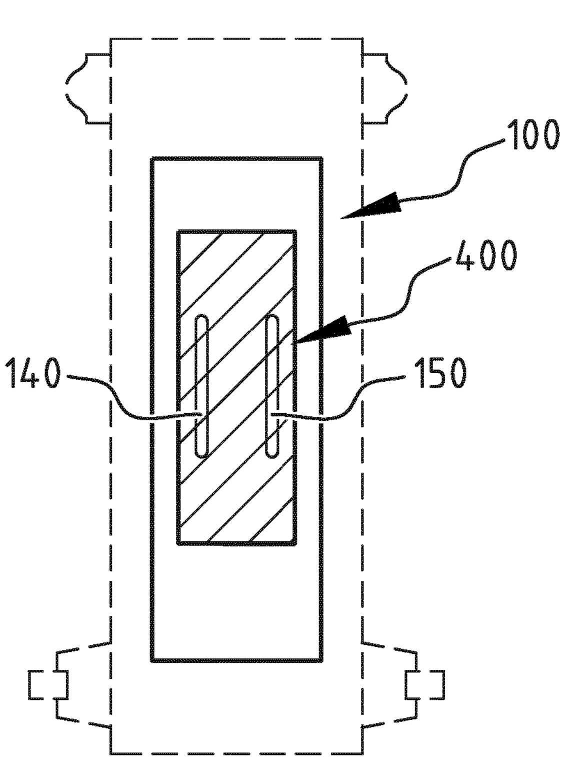
FIG. 5
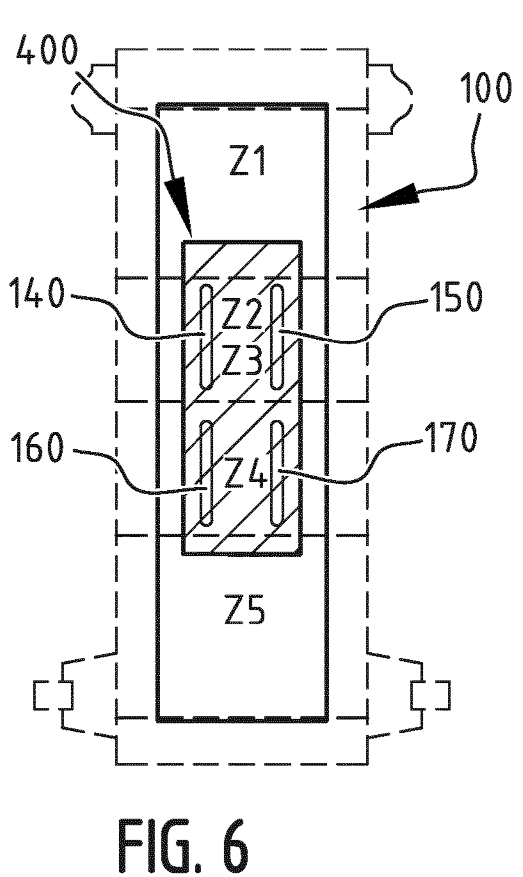
FIG. 6

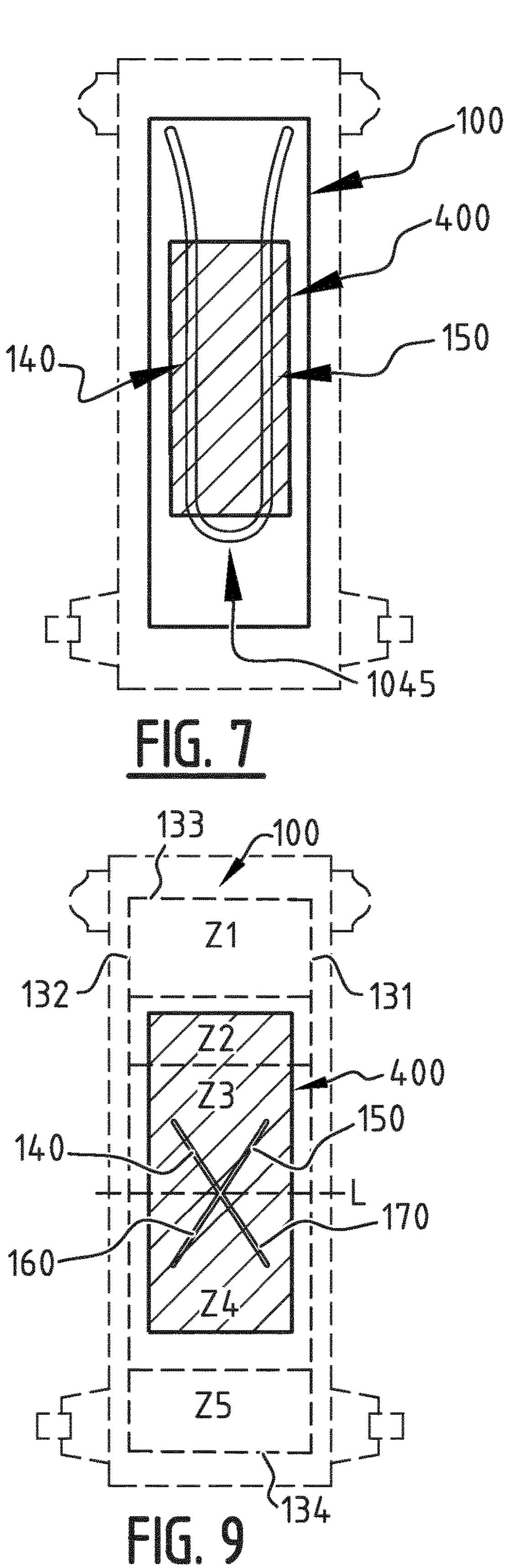
100
400
140
150
1045
FIG. 7
133
100
Z1
132
131
Z2
400
Z3
140
150
L
160
170
Z4
Z5
134
FIG. 9
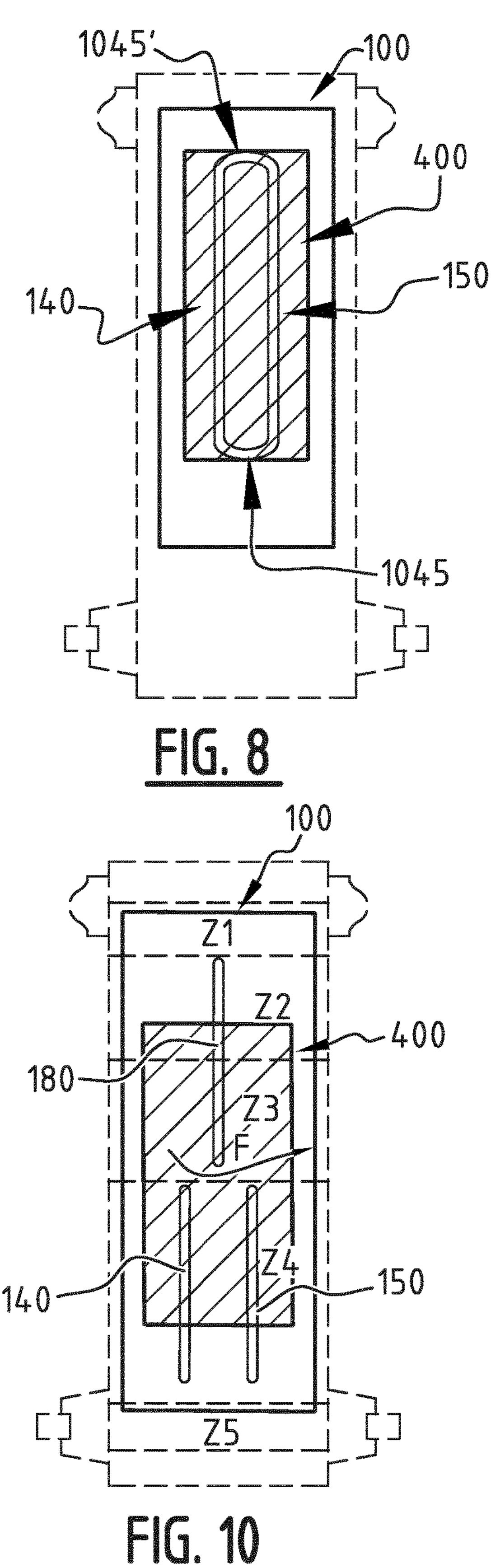
1045'
100
400
140
150
1045
FIG. 8
100
Z1
Z2
400
180
Z3
F
Z4
140
150
Z5
FIG. 10

31
31'
E

E d3
α

E
d4
d2
d1
d3
1000
E d1
1010
SECTION E-E

ABSORBENT ARTICLE WITH IMPROVED BOTTOM DISTRIBUTION ASSEMBLY

PRIORITY APPLICATIONS

This application is a U.S. National Stage Filing under 35 U.S.C. § 371 from International Application No. PCT/EP2021/083004, filed on Nov. 25, 2021, and published as WO2022/128391 on Jun. 23, 2022, which claims the benefit of priority to Netherlands Application No. 2027163, filed on Dec. 18, 2020; the benefit of priority of each of which is hereby claimed herein, and which applications and publication are hereby incorporated herein by reference in their entireties.

TECHNICAL FIELD

The present invention pertains to the technical field of absorbent articles, more preferably disposable personal care articles such as diapers, baby pants, adult incontinent garments, and the like, and to absorbent structures for use in such absorbent articles. More specifically the present invention relates to an absorbent article comprising an absorbent core with one or more channels between a topsheet and a backsheet. The present invention also relates to methods for manufacturing such an absorbent article.

BACKGROUND

Absorbent articles comprising an absorbent core with one or more channels between a topsheet and a backsheet are well known. Examples of such absorbent articles are described for example in patents EP 3 403 630 B1, EP 3 403 632 B1 and EP 3 403 631 A1 in the name of the applicant, which are incorporated herein by reference.

It is known to include a liquid-impermeable, either hydrophilic or hydrophobic, distribution or wicking layer which helps to wick and transport liquids and having a capability to disperse the liquid over the surface of said wicking layer from the less absorbent area's (e.g. saturated) to the more absorbent area's (e.g. unsaturated). The distribution layer or wicking layer is preferably located at the garment facing side of the absorbent core. Due to the specific absorbent capacity of the distribution or wicking layer, the liquid in the one or more channels will be drawn up into the distribution layer and will spread out throughout the rest of the distribution layer. In that way, the distribution, transport and absorption of the liquid can be improved.

It is further known to provide a liquid distribution and acquisition layer (ADL) between the topsheet and the absorbent core in order to take up and distribute the liquid from the topsheet towards the absorbent core. Typically, an ADL extends over an area where liquid insult is to be expected. Known ADL layers have the disadvantage that it takes some time before a dry feeling is obtained at the topsheet surface and that rewetting can be significant.

SUMMARY

The object of embodiments of the invention is to provide an absorbent article of the type stated in the preamble, with an improved bottom distribution between the absorbent material and the backsheet, whilst maintaining a good integrity of the absorbent article.

According to a first aspect of the invention, there is provided an absorbent article comprising a liquid pervious topsheet, a liquid impervious backsheet, absorbent material positioned between the liquid pervious topsheet and the liquid impervious backsheet, and a bottom distribution assembly between the absorbent material and the liquid impervious backsheet. The absorbent material comprises superabsorbent polymer particles and is arranged such that one or more channels are formed, wherein less absorbent material per surface area is present in the one or more channels compared to an area around the one or more channels, wherein preferably substantially no absorbent material is present in the one or more channels. The bottom distribution assembly comprises a first layer and a second layer, wherein said first layer has a first density between 20 and 150 kg/m3 and said second layer has a second density between 100 and 400 kg/m3, said second density being higher than the first density, wherein said first layer is closer to the absorbent material than said second layer.

By providing a bottom distribution assembly with a first and second layer as defined above, the first layer can be used for distribution purposes, distributing the liquid from the one or more channels to the absorbent material, whilst the second layer provides integrity to the absorbent article. The liquid may be transported from the one or more channels through the first layer, along areas where the absorbent material is saturated, e.g. areas close to the one or more channels, to other areas where the absorbent material is not yet saturated. Thus, the first layer may function as a porous wicking layer. The second layer may form a barrier for the superabsorbent polymer particles and may be connected in the channels to other sheets in the absorbent article, such as the top core wrap sheet and/or the capillary acceleration sheet, e.g. by sealing or gluing. Because of the higher density of the second layer such connection will be more robust with less risk of superabsorbent particles negatively influencing the attachment. In that way the absorbent article can better maintain its structure, also after wetting.

Preferably, the bottom distribution assembly consists of a single sheet. In that way the bottom distribution assembly can be easily transported in a machine for producing the absorbent articles. Further, the strength and/or integrity of the absorbent article may be increased.

Preferably, the bottom distribution assembly is in direct contact with the superabsorbent particles. Thus, by using a bottom distribution assembly, a bottom core wrap sheet may be omitted. Thus, the bottom distribution assembly may also play a role in wrapping the absorbent material.

Preferably, a difference between the first and the second density is higher than 20 kg/m3, more preferably higher than 30 kg/m3 even more preferably higher than 40 kg/m2, even more preferably between 50 and 150 kg/m3, most preferably between 60 and 140 kg/m3, e.g. between 70 and 130 kg/m3. By using such differences in density a good balance between distribution and integrity properties can be achieved.

In an exemplary embodiment, the first layer is a spunbond layer and the second layer is a spunbond layer. Thus, the first layer may be a more porous spunbond layer than the second layer. The first and second layer may be obtained using multiple spinning column, whereupon the assembly is interconnected using e.g. through-air-bonding.

In another exemplary embodiment, the first layer is a through-air-bonded carded non-woven and the second layer is a spunbond layer, e.g. a PP spunbond layer.

In an exemplary embodiment, the bottom distribution assembly is a through-air bonded non-woven. This may be an spunbond/spunbond through-air-bonded nonwoven obtained as described above, or a classical through-air bonded nonwoven obtained by sequentially feeding the fibres of the first and second layer.

In a preferred embodiment, the first layer has a first basis weight and the second layer has a second basis weight, said second basis weight being lower than said first basis weight. Thus, the second layer may be a rather thin layer as it does not have to contribute to the distribution. Preferably, the difference between the first layer and the second layer is larger than 1 g/m2, more preferably larger than 2 g/m2, even more preferably larger than 3 g/m2, or even larger than 5 g/m2, for example between 1 and 10 g/m2.

In an exemplary embodiment, the first layer has a first basis weight between 15 and 80 g/m2, preferably between 25 and 80 g/m2, and/or the second layer has a second basis weight between 8 and 35 g/m2, preferably between 8 and 25 g/m2.

Preferably, the first layer and/or the second layer comprise more than 90 weight % of synthetic fibres, preferably more than 95 weight % of synthetic fibres.

In a preferred embodiment, the first layer comprises polyester fibres. Polyester fibres have the advantage of being capable of providing a highly voluminous first layer, resulting in good distribution properties.

In a possible embodiment, the second layer comprises any one of the following fibres or a combination thereof: polyethylene, polyester, copolyester, polypropylene, polyactic acid (PLA).

Preferably, the second density is selected such that it forms a barrier for the superabsorbent particles. For example, the second layer may have a mean flow pore size below a predetermined value, and the absorbent material comprises superabsorbent particles prepared such that substantially no superabsorbent particles having dimensions smaller than said mean flow pore size are present in the absorbent material. By using absorbent material comprising absorbent particles with a well-defined particle size distribution (PDS) adapted to the flow pore size of the bottom distribution assembly, and in particular the second layer thereof, any escaping of absorbent material can be reduced. Topping of the fines (e.g. a "dust-fraction"<50 μm) away may be advantageous, as well as the removal of large fraction (e.g. >600 μm). For example, traditional blend polymerization superabsorbent particles can serve for this purpose, with sieve selection. According to another example drop polymerization superabsorbent particles (e.g. SAVIVA® superabsorbent of the company BASF) with a narrow PDS can be used. Also solvent polymerized superabsorbent particles can have such a narrow PDS.

In an exemplary embodiment, the mean flow pore size of the bottom distribution assembly is below 200 micron, more preferably below 150 micron, even more preferably between 10 and 150 micron, and most preferably between 20 and 150 micron. These values may be achieved thanks to the presence of the second layer.

In an exemplary embodiment, the absorbent article further comprises a top core wrap sheet and/or a capillary acceleration sheet between the absorbent material and the topsheet. Preferably, the bottom distribution assembly is attached to the top core wrap sheet and/or the capillary acceleration at least in a portion of the one or more channels. In that manner, a well structured absorbent article is obtained with one or more well defined channels, further improving the liquid guidance by mass flow through the one or more channels, through the bottom distribution assembly to the absorbent material.

Preferably, the bottom distribution sheet is attached along a periphery to the bottom core wrap sheet and/or the capillary acceleration sheet.

In an exemplary embodiment, the bottom distribution assembly is glued to the top core wrap sheet and/or a capillary acceleration at least in a portion of the one or more channels. For example, adhesive may be arranged in one or more lanes or in a swirl pattern on the top core wrap sheet and/or the capillary acceleration sheet and/or the bottom distribution assembly, such that the one or more lanes or swirl pattern overlap at least partially with the one or more channels. Since the first layer is a relatively porous layer it will allow glue to pass through the first layer to be adhered to the second layer.

In addition or alternatively, the bottom distribution assembly is sealed in accordance with a sealing pattern to the top core wrap sheet and/or to the capillary acceleration at least in a portion of the one or more channels, wherein preferably the sealing is realized by heat and/or pressure and/or ultrasonic energy. For example, the sealing pattern covers less than 80%, preferably less than 70%, more preferably less than 60%, even more preferably less than 50%, most preferably between 1 and 50% of the surface area of the one or more channels. For example, the sealing pattern covers between 1 and 50% of the total surface area of the one or more channels, or between 1 and 40%, or between 1 and 30%, or between 1 and 25%, or between 2 and 25%, or between 3 and 25%, or between 4 and 25%.

Such sealing pattern can provide a good resistance against the swell forces generated by liquid being captured in the superabsorbent particles by hydrogen bonds, but the sealing pattern equally can provide resistance against dry and wet superabsorbent particles trying to penetrate through the second layer and through the sealing pattern after as well as during the sealing step of the manufacturing process. In that manner, any risk of dry or wet SAP particles coming into contact with sensitive skin upon wearing is avoided or reduced. Further, by having a reduced surface area that is being sealed in accordance with a pattern, any particles remaining in the one or more channel zones can easily migrate to a non-sealing area so that the risk of creating holes in the one or more channel zones is reduced or avoided.

Preferably, the sealing pattern is a regular pattern, such as a line pattern such as a grid, a pattern of dots, etc. The dots may have any shape, e.g. round, polygonal, etc. The line pattern may comprise one or more sets of parallel lines. When a first set of parallel lines and a second set of parallel lines is included, the lines of the first set may be oriented at a non-zero angle with respect to the lines of the second set.

Preferably, the sealing pattern comprises a large number of distinct sealing areas spread across the one or more channels. Preferably, the large number is larger than 10, more preferably larger than 20.

Preferably, the sealing pattern comprises a plurality of discrete elements, and each discrete element has a first dimension in a first direction and a second dimensions in a direction perpendicular to the first direction. The first dimension is smaller than 2 mm, preferably smaller than 1.5 mm, more preferably smaller than 1 mm, e.g. between 0.1 and 0.7 mm or between 0.2 and 0.7 mm, or between 0.3 and 0.6 mm.

By providing well selected sealing patterns, such as grids, dots, polygons, etc., that have a limited total bonding area with fine single bonding areas, e.g. having a surface area smaller than 2 $mm^2$ or a line thickness lower than 1 mm, individual superabsorbent particles will find easier their way to non-sealed zones in order not to create any hole.

According to second aspect there is provided an absorbent article comprising a liquid pervious topsheet, a liquid impervious backsheet, absorbent material positioned between the liquid pervious topsheet and the liquid impervious backsheet, and a bottom distribution assembly between the absorbent material and the liquid impervious backsheet, wherein the absorbent material comprises superabsorbent particles and is arranged such that one or more channels are formed, wherein less absorbent material per surface area is present in the one or more channels compared to an area around the one or more channels, wherein preferably substantially no absorbent material is present in the one or more channels, wherein the bottom distribution assembly comprises a spunbond layer and a meltblown layer, wherein said spunbond layer comprises polyester fibres, wherein the spunbond layer is arranged closer to the absorbent material than the meltblown layer.

Preferably, the bottom distribution assembly is a spunbond meltblown spunbond nonwoven comprising the spunbond layer, the meltblown layer and a second spunbond layer on the other side of the meltblown layer.

In an exemplary embodiment the spunbond layer has a basis weight between 10 and 80 g/m2, preferably between 10 and 50 g/m2, for example, between 15 and 50 g/m2.

In an exemplary embodiment the meltblown layer has a basis weight between 1 and 10 g/m2, preferably between 2 and 10 g/m2, for example, between 3 and 10 g/m2.

In an exemplary embodiment the second spunbond layer has a basis weight which is lower than the basis weight of the spunbond layer, e.g. between 5 and 30 g/m2, preferably between 5 and 20 g/m2, for example, between 5 and 15 g/m2.

In an exemplary embodiment the second spunbond layer comprises polypropylene fibres.

In a preferred embodiment, the absorbent article further comprises a capillary acceleration sheet and/or a top core wrap sheet between the topsheet and the absorbent material, wherein the bottom distribution assembly is attached to the capillary acceleration sheet and/or the top core wrap sheet at least in a portion of the one or more channels, preferably according to a sealing pattern, e.g. a sealing pattern as disclosed above for the first aspect.

Other preferred features of the first aspect may also be combined with the second aspect.

For determining the density of the bottom distribution assembly, the mass per unit area may be measured using NWSP 130.1.R0 (20) and the nonwoven thickness may be measured using NWSP 120.6.R0 (15). The density can then be calculated as the mass per unit area divided by the thickness.

The capillary acceleration sheet may comprise at least one meltblown layer, preferably a single meltblown layer. The at least one meltblown layer represents between 2 and 30 weight % of the weight of the capillary acceleration sheet, preferably between 3 and 30 weight %, more preferably between 3 and 20 weight %, even more preferably between 3 and 18 weight %. For example, the at least one meltblown layer represents between 3 and 15 weight %, between 3 and 14 weight %, between 3 and 13 weight %, between 3 and 12 weight, between 3 and 11 weight % or between 3% and 10 weight %. In addition or alternatively, the at least one meltblown layer, preferably a single meltblown layer, has a basis weight of less than 6 g/m$^2$, preferably less than 5 g/m$^2$, more preferably less than 4 g/m$^2$, even more preferably less than 3 g/m$^2$, e.g. less than 2 g/m$^2$. For example, the at least one meltblown layer has a basis weight between 0.5 g/m$^2$ and 5 g/m$^2$, or between 0.5 g/m$^2$ and 4 g/m$^2$, between 0.5 g/m$^2$ and 3 g/m$^2$, or between 0.4 g/m$^2$ and 2 g/m$^2$.

In that way a good topsheet dryness, and in particular a fast topsheet dryness after liquid insult, and a good rewetting behaviour, is obtained, whilst avoiding that absorbent material, and in particular superabsorbent particles, escape from the absorbent article and/or contact the skin of the wearer of the absorbent article. By having a small melt fraction in the capillary acceleration sheet, the absorbent material, and in particular super absorbent particles can be well maintained in the absorbent article without requiring an adapted topsheet or other layer. On the other hand, since the melt fraction is low, the remaining fraction of the capillary acceleration sheet can fulfil its capillary acceleration function. By combining at least one channel with a capillary acceleration sheet a fast dryness feeling and a low rewetting at the level of the topsheet can be ensured, whilst at the same time providing a good liquid distribution through the one or more channels resulting in improved leakage protection. Also, the topsheet may be an apertured topsheet as the melt fraction of the capillary acceleration sheet will avoid that any significant amounts of absorbent material, and in particular of superabsorbent particles, escape through the topsheet.

In an exemplary embodiment, the capillary acceleration sheet has a mean flow pore size below a predetermined value, and the absorbent material comprises superabsorbent particles prepared such that substantially no superabsorbent particles having dimensions smaller than said mean flow pore size are present in the absorbent material. By using absorbent material comprising absorbent particles with a well-defined particle size distribution (PDS) adapted to the flow pore size of the capillary acceleration sheet, any escaping of absorbent material through the topsheet can be further reduced. Topping of the fines (e.g. a "dust-fraction" <50 μm) away may be advantageous, as well as the removal of large fraction (e.g. >600 μm). For example, traditional blend polymerization superabsorbent particles can serve for this purpose, with sieve selection. According to another example drop polymerization superabsorbent particles (e.g. SAVIVA® superabsorbent of the company BASF) with a narrow PDS can be used. Also solvent polymerized superabsorbent particles can have such a narrow PDS.

Preferably, the capillary acceleration sheet consists of a spunbond meltblown nonwoven fabric or a spunbond-meltblown-spunbond nonwoven fabric.

Preferably, the capillary acceleration sheet comprises a spunbond layer arranged against the topsheet. For example, the capillary acceleration sheet may consist of a spunbond meltblown nonwoven fabric, SM, with a spunbond layer thereof facing the topsheet and a meltblown layer thereof facing the absorbent material. In an embodiment without a top core wrap sheet, the meltblown layer may be in direct contact with the absorbent material. In an embodiment with a top core wrap sheet, the meltblown layer may be in direct contact with the top core wrap sheet.

The capillary acceleration sheet may have a mean flow pore size below 50 micron, preferably between 5 and 50 micron, more preferably between 10 and 50 micron, e.g. between 10 and 40 micron or between 20 and 40 micron.

By having a capillary acceleration sheet with a mean flow pore size below 50 micron, the absorbent material, and in particular super absorbent particles can be well maintained in the absorbent article without requiring an adapted topsheet. On the other hand, the capillary acceleration sheet can fulfil its capillary acceleration function, and will allow liquid to pass through the capillary acceleration sheet. By combining at least one channel with a capillary acceleration sheet a fast dryness feeling and a low rewetting at the level of the topsheet can be ensured, whilst at the same time providing a good liquid distribution through the one or more channels resulting in improved leakage protection. Also, the topsheet may be an apertured topsheet as the low mean flow pore size of the capillary acceleration sheet will avoid that any significant amounts of absorbent material, and in particular of superabsorbent particles, escape through the topsheet.

The measure "mean flow pore size" refers to a measure of average pore diameter as determined by a liquid displacement technique utilizing a Coulter Porometer and Coulter POROFIL® test liquid available from Coulter Electronics Limited, Luton, England. The mean flow pore size is determined by wetting a test sample with a liquid having a very low surface tension (i.e., Coulter POROFIL®). Air pressure is applied to one side of the sample. Eventually, as the air pressure is increased, the capillary attraction of the fluid in the largest pores is overcome, forcing the liquid out and allowing air to pass through the sample. With further increases in the air pressure, progressively smaller and smaller holes will clear. A flow versus pressure relationship for the wet sample can be established and compared to the results for the dry sample. The mean flow pore size is measured at the point where the curve representing 50% of the dry sample flow versus pressure intersects the curve representing wet sample flow versus pressure. The diameter of the pore which opens at that particular pressure (i.e., the mean flow pore size) can be determined from the following expression: pore diameter $\mu$m=40 $\tau$/pressure, where $\tau$=surface tension of the fluid expressed in units of mN/M; the pressure is the applied pressure expressed in millibars (mbar); and the very low surface tension of the liquid used to wet the sample allows one to assume that the contact angle of the liquid on the sample is about zero.

The capillary acceleration sheet may have a mean flow pore size below a predetermined value, and the absorbent material comprises superabsorbent particles prepared such that substantially no superabsorbent particles having dimensions smaller than said mean flow pore size are present in the absorbent material.

By using a capillary acceleration sheet having a mean flow pore size below a predetermined value in combination with absorbent particles with a well-defined particle size distribution (PDS) adapted to the predetermined value, any escaping of absorbent material through the topsheet can be avoided or reduced. For example, traditional blend polymerization superabsorbent particles can serve for this purpose, wherein a sieve selection is used to obtain the desired PDS. According to another example drop polymerization superabsorbent particles (e.g. SAVIVA® superabsorbent of the company BASF) with a narrow PDS can be used. Also solvent polymerized superabsorbent particles can have such a narrow PDS.

Preferably, the mean flow pore size is between 10 and 200 micron, more preferably between 10 and 150 micron, even more preferably between 20 and 150 micron, and most preferably between 30 and 150 micron. For example, the mean flow pore size is between 30 and 120 micron or between 30 and 100 micron.

In an exemplary embodiment, the absorbent article comprises a top core wrap sheet arranged between the capillary acceleration sheet and the absorbent material, and the capillary acceleration sheet is sealed to the top core wrap sheet according to the sealing pattern, and optionally also to the bottom core wrap sheet through the top core wrap sheet.

Preferably, the sealing is realized by heat and/or pressure and/or ultrasonic energy. Preferably, the sealing is done by pressing one or more sealing bars against one or more zones overlapping with the one or more channels, said sealing bars being provided with protrusions according to the sealing pattern.

In an exemplary embodiment, the capillary acceleration sheet consists of a spunbond nonwoven fabric.

In another exemplary embodiment, the capillary acceleration sheet consists of a spunbond meltblown nonwoven fabric or a spunbond-meltblown-spunbond nonwoven fabric.

Preferably, the capillary acceleration sheet has a basis weight between 5 and 55 g/m2, more preferably between 7 and 45 g/m2, even more preferably 8 and 30 g/m2, e.g. between 9 and 20 g/m2. Such basis weight, optionally in combination with the relatively fine fibres in the capillary acceleration sheet, provide for an adequate capillary suction force with low rewetting. More in particular, the liquid is sucked in very fast and is allowed to be distributed by the one or more channels and to be absorbed by the absorbent material reducing the chances of rewetting the top layer.

The basis weight may be measured using the ISO 9073-1 test method.

Preferably, the capillary acceleration sheet is a nonwoven comprising fibres having an average diameter between 10 and 35 micron, more preferably between 15 and 30 micron, even more preferably between 17 and 27 micron.

More in particular, the capillary acceleration sheet may have a fineness which results in a high capillary suction of liquid towards the absorbent material, where the liquid is further distributed through the at least one channel and absorbed by the absorbent material. Thus, the capillary acceleration sheet pulls liquid to the absorbent material in a very fast manner, resulting in a fast dryness at top sheet level.

In an exemplary embodiment, the capillary acceleration sheet has an average fineness which is between 2-6 dtex, i.e. between 1.8 and 5.4 den. It is noted that instead of or in addition to defining the average diameter of the capillary acceleration sheet, this sheet may also be defined using a fineness value, such as a dtex value or a den value. A den value may be determined using test method ASTM 1577.

Preferably, the capillary acceleration sheet is attached to the bottom core distribution assembly at least in a portion of the one or more channels. The attachment may be a continuous or discontinuous attachment. For example, the capillary acceleration sheet may be attached to the bottom distribution assembly along a major portion of the one or more channels, with one or more unattached portions being present between attached portions. The one or more channels may comprise one or more permanent attachment portions which remain attached after wetting and/or one or more semi-permanent attachment portions which detach after wetting and/or one or more unattached portions. An unattached portion or a semi-permanent attachment portion allows for an increased swelling of the absorbent material after the one or more channels have fulfilled their function of distributing the liquid, as wet absorbent material is allowed to extend/swell into the channel area in case of an unattached or detached portion.

More preferably, no additional sheet is present between the superabsorbent particles and the capillary acceleration sheet. In such an embodiment, the absorbent core can thus be formed by the bottom distribution assembly, the capillary acceleration sheet, and the absorbent material included between the capillary acceleration sheet and the bottom distribution assembly.

Preferably, the absorbent material extends over a surface area of the bottom distribution assembly, and the capillary acceleration sheet extends over the full surface area of the absorbent material. The capillary acceleration sheet may be attached along a periphery to the bottom distribution assembly.

Thus the capillary acceleration sheet may fulfil the role of top core wrap sheet whilst at the same time providing a capillary structure configured for ensuring a fast dryness of the topsheet.

Even more preferably, no additional sheet is present between the topsheet and the capillary acceleration sheet. Thus, the capillary acceleration sheet can also fulfil the role of acquiring and distributing the liquid, and does this by fast capillary suction.

According to another possible embodiment, the absorbent article further comprises a top core wrap sheet arranged between the capillary acceleration sheet and the absorbent material. The top core wrap sheet may then be attached to the bottom distribution assembly at least in a portion of the one or more channels, and the capillary acceleration sheet may be attached to the top core wrap sheet in at least a portion of the one or more channels. When such an embodiment is used, the capillary acceleration sheet may be smaller than the bottom distribution assembly, and may be present where liquid insult is to be expected. It is further noted that the top and bottom distribution assembly may be two separate sheets or one sheet wrapping the absorbent material of the absorbent core.

According to an exemplary embodiment, the capillary acceleration sheet is a nonwoven with polypropylene (PP) fibres. The advantage of PP is that it can be easily shaped.

According to an exemplary embodiment, the topsheet is an apertured topsheet having apertures with a surface area larger than 0.1 mm2, preferably larger than 0.5 mm2. This allows liquid to pass easily through the topsheet towards the capillary acceleration sheet. Especially for embodiments where the capillary acceleration sheet forms a barrier for superabsorbent particles such an embodiment is advantageous.

Optionally, a bottom core wrap sheet may be arranged between the bottom distribution assembly and the absorbent material, but typically this is not preferred. Such bottom core wrap sheet may have a specific volume above 15 g/m2.

According to an exemplary embodiment, the capillary acceleration sheet comprises a blend of fibres having different diameters. Preferably, the fibres are intermingled, i.e. preferably the different fibres are not arranged in layers but mixed with each other to form the capillary acceleration sheet. Preferably, a blend of polypropylene (PP) fibres is used. However, it is also possible to use other single component or bi-component fibres, such as polyethylene (PE) fibres, polyethylene-terephthalate (PET) fibres, PE/PP bi-component fibres, PE/PLA bi-component fibres, etc. The fibres may be continuously crimped fibres.

According to an exemplary embodiment, the capillary acceleration sheet comprises a blend of first fibres having an average first diameter above 20 micron, preferably above 22 micron, more preferably above 24 micron, and second fibres having an average second diameter below 20 micron, preferably below 19 micron, more preferably below 18 micron. In that manner, the fine second fibres will contribute to the fast capillary suction whilst the coarser first fibres will ensure a good distribution of the liquid, also by mass flow.

Preferably, the first fibres represent less than 50 weight % of the capillary acceleration sheet, more preferably less than 45 weight %, and the second fibres represent more than 50 weight % of the capillary acceleration sheet, more preferably more than 55 weight %. Such a distribution provides a good balance between suction and migration by capillary flow promoted by the finer second fibres and liquid distribution by mass flow promoted by the coarser first fibres.

According to an exemplary embodiment, the capillary acceleration sheet is a continuous filament web. The capillary acceleration sheet may be a spunbond nonwoven, a carded nonwoven, a spunlace nonwoven. The capillary acceleration sheet may be made by spunbonding, carding, or spunlacing (hydro-entangling), or a combination thereof. If the capillary acceleration sheet is a spunbond web, it may be a calandered (i.e. a point bonded) spunbond web, preferably with a bonding area between 10 and 30%.

According to an exemplary embodiment, the capillary acceleration sheet comprises a fraction of fibres having an average diameter which is at least 10% lower than an average diameter of the fibres of the liquid pervious topsheet, preferably at least 20% lower than an average diameter of the fibres of the liquid pervious topsheet. By having finer fibres in the capillary acceleration sheet than in the topsheet, the liquid will pass fast through the topsheet and the main capillary suction will take place in the capillary acceleration sheet.

- Preferably, the topsheet has a basis weight between 10 and 30 g/m$^2$, preferably between 15 and 25 g/m$^2$. Preferably, the fibres of the topsheet have an average fineness between 1-3 dtex.
- Preferably, the topsheet is any one of the following: a spunbond nonwoven, a through air bonded carded web (TABCW). Preferably, the through air bonded carded web comprises polyethylene/polypropylene bi-component staple fibres.

According to an exemplary embodiment, at least a portion of the topsheet is bonded to the capillary acceleration sheet, preferably at least in a portion of the one or more channels.

According to an exemplary embodiment, the capillary acceleration sheet extends over at least 15%, preferably at least 20%, more preferably at least 45% of an upper surface area of the bottom distribution assembly; and/or wherein he capillary acceleration sheet extends over at least 25%, preferably at least 30%, more preferably at least 35% of a length of the bottom distribution assembly; and/or wherein the capillary acceleration sheet extends over at least 25%, preferably at least 30%, more preferably at least 35% of a width of the bottom distribution assembly. As explained above, in a preferred embodiment, the capillary acceleration sheet may extend over the entire upper surface of the bottom distribution assembly and may fulfil the function of a top core wrap sheet.

According to an exemplary embodiment, the bottom distribution assembly has a first and second longitudinal edge and a first and second transverse edge and the one or more channels comprise at least one elongate channel extending from a crotch region in the direction of the first and/or second transverse edge. Such channels will allow a good liquid distribution by mass flow between the first and second transverse edge.

According to an exemplary embodiment, the one or more channels comprise one or more attachment zones where the capillary acceleration sheet and/or the top core wrap sheet, if present, is attached to the back core wrap sheet. Preferably, the one or more attachment zones are formed by any one of the following or a combination thereof: pressure bonding, thermal bonding, sonic bonding, chemical bonding, adhesive. According to an exemplary embodiment, the one or more channels comprise any one or more of the following: one or more permanent attachment zones, one or more semi-permanent attachment zones configured to release after having been in contact with liquid, for example after having been in contact with the liquid for a time period of less than 2 minutes, one or more unattached zones.

According to an exemplary embodiment, a width of the one or more channels, seen in a transverse direction of the bottom distribution assembly, is at least 1 mm, preferably at least 2 mm, more preferably at least 3 mm, most preferably at least 4 mm. In that manner, it can be ensured that a sufficient amount of liquid can be distributed and any leakage can be limited or avoided.

According to an exemplary embodiment, the one or more channels comprise a first channel and a second channel which extend next to each other and are each extending in the direction of a first and/or second transverse edge of the bottom distribution assembly. Preferably, the first and second channel are oriented substantially in a longitudinal direction of the bottom distribution assembly.

Preferably, the capillary acceleration sheet at least partially covers the first and second channel. In that manner, the capillary acceleration sheet can suck liquid towards the two channels.

According to an exemplary embodiment, the distance between the first and the second channel is between 10 mm and 50 mm, preferably between 15 mm and 30 mm; and/or the length of the first and the second channel is larger than 60 mm, preferably larger than 70 mm. Such dimensions will typically result in a good distribution. The skilled person understands that the dimensions will be dependent on the size of the absorbent article, and thus one the size of the bottom distribution assembly.

According to an exemplary embodiment, the one or more channels further comprise a third and a fourth channel located at a distance of each other and at a distance of the first and second channel, said third and fourth channel each extending in the direction of the first and/or second transverse edge. Preferably, the capillary acceleration sheet at least partially covers the third and fourth channel. By adding such a third and fourth channel the distribution can be further enhanced.

- Preferably, the distance between the first and the second channel is different from the distance between the third and the fourth channel.
- Preferably, the bottom distribution assembly has a front portion extending at one side of a transverse crotch line and a rear portion extending at the other side of the transverse crotch line; wherein the first and second channel extend at least in the front portion of the bottom distribution assembly; and wherein the third and fourth channel extend at least in the rear portion of the bottom distribution assembly. Preferably, the distance between the first and the second channel is smaller than the distance between the third and the fourth channel.
- Optionally, the first channel may be connected to the third channel through a first semi-permanent attachment zone and the second channel may be connected to the fourth attachment zone through a second semi-permanent attachment zone, wherein the first, second, third and fourth channels are formed by permanent attachment zones.

According to an exemplary embodiment, the one or more channels comprise at least a first and a second attachment zone located a distance of each other, said first and second attachment zone each extending from a crotch region in the direction of a first and/or second transverse edge of the bottom distribution assembly.

According to an exemplary embodiment, a position and/or shape of the one or more channels is indicated by means of a distinguishable colour and/or coloured pattern, e.g. by a printed ink layer.

For example, the distinguishable colour and/or coloured pattern may be provided on at least one of the topsheet, the capillary acceleration sheet, the backsheet and the bottom distribution assembly.

According to an exemplary embodiment, the one or more channels together extend over a channel length which is at least 20%, preferably at least 30%, preferably at least 40%, more preferably at least 50% of a length of the bottom distribution assembly.

According to an exemplary embodiment, the one or more channels and the capillary acceleration sheet are arranged symmetrically with respect to a longitudinal centre line of the bottom distribution assembly.

Preferably, the absorbent material comprises cellulosic fluff pulp made up of cellulose fibres and superabsorbent particles. The fibres can be natural or synthetic. According to another exemplary embodiment, the absorbent material is substantially fluffless. Typically, absorbent material refers to a material that is applied in bulk, i.e. a 3D absorbent material, i.e. not as a sheet. In some embodiments, the absorbent material may comprise more than 20 weight % superabsorbent particles or more than 40 weight % superabsorbent particles or more than 60 weight % superabsorbent particles, or more than 80 weight % superabsorbent particles. The absorbent material may also be fluffless, i.e. with substantially without cellulose fibres.

According to another aspect there is provided a method for manufacturing an absorbent article. The method comprises the steps of providing a liquid pervious topsheet and a liquid impervious backsheet; arranging an absorbent material, typically comprising superabsorbent particles, between a bottom distribution assembly, on one side, and a top core wrap sheet and/or a capillary acceleration sheet, on the other side, such that one or more channels are formed, wherein less absorbent material per surface area is present in the one or more channels compared to areas around the one or more channels, wherein preferably substantially no absorbent material is present in the one or more channels; and arranging the liquid pervious topsheet at the side of top core wrap sheet and/or the capillary acceleration sheet and the liquid impervious backsheet at the side of the bottom distribution assembly, wherein the bottom distribution assembly has any one or more of the features defined above.

Preferably, the arranging of the absorbent material comprises the steps of guiding a first sheet material along a rotating member, wherein a surface of said rotating member is provided with a pattern with suction zones and non-suction zones; wherein said non-suction zones comprise one or more channel zones; applying an absorbent material on said first sheet material on the rotating member such that the suction zones are covered with absorbent material and substantially no absorbent material is present on the non-suction zones; and applying a second sheet material on top of the absorbent material on the first sheet material; and at least partially attaching said first sheet material to said second sheet material in the areas where substantially no absorbent material is present, such that one or more channels are formed. One of said first and second sheet material is a material for forming the capillary acceleration sheet and/or the top core wrap sheet, and the other one is a material for forming the bottom distribution assembly.

Preferably, the attaching is done by applying pressure and/or heat and/or ultrasonic energy on the bottom distribution assembly and on at least one of the capillary acceleration sheet material and the top core wrap sheet material (depending on which one is present) in the areas where substantially no absorbent material is present. For example, a sealing pattern as described above may be used for the attaching. Optionally the sealing with a sealing pattern may be combined with applying an adhesive between the capillary acceleration sheet material and/or top core wrap sheet, on the one hand, and the bottom distribution assembly on the other hand.

Any of the features described above in connection with the absorbent article are also applicable for embodiments of the method.

BRIEF DESCRIPTION OF FIGURES

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which:

FIGS. 3-10 are schematic top plan views of exemplary embodiments of a diaper;

DESCRIPTION OF EMBODIMENTS

Figures 1A, 1B, 1C:
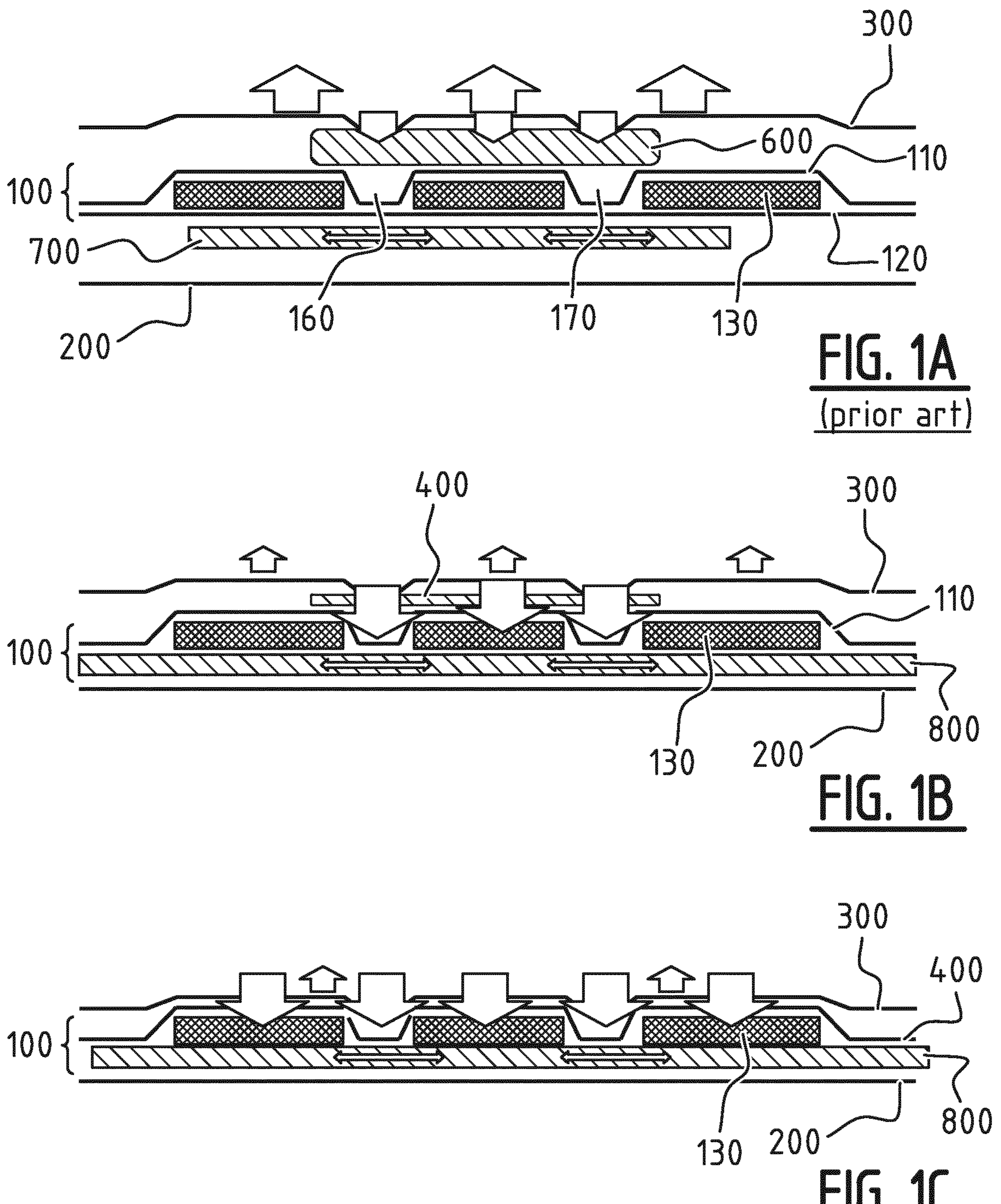
FIG. 1A is a schematic cross-section of an exemplary embodiment of an absorbent article with an absorbent core according to the prior art.
FIGS. 1B and 1C and 1D are cross-sections of exemplary embodiments of an absorbent article with an absorbent core according to the invention.
Figures 2A, 2B, 2C:
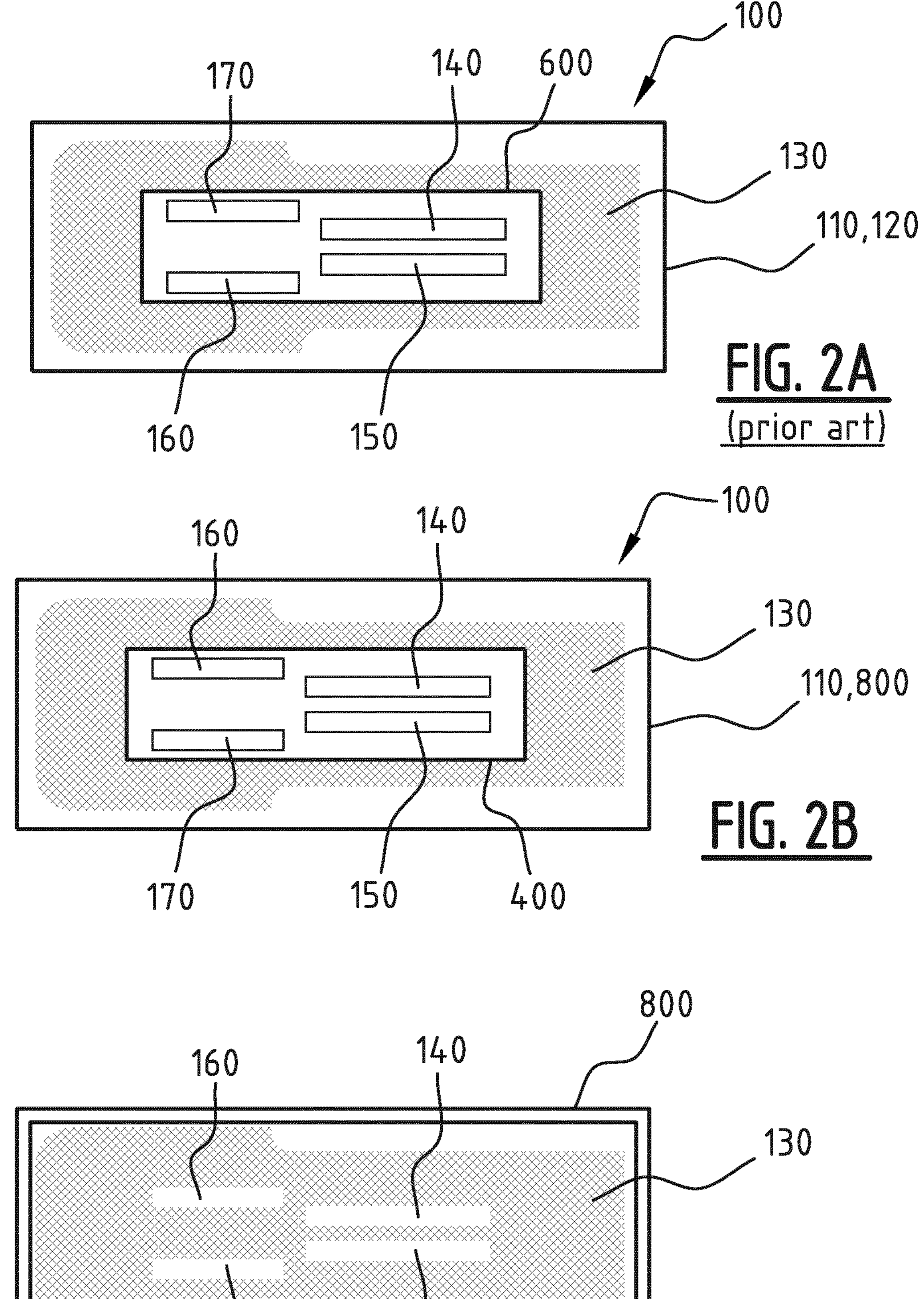
FIGS. 2A-2C are schematic top views of the absorbent core of the exemplary embodiments of FIGS. 1A-1C, respectively.

FIGS. 1A and 2A show an exemplary embodiment of an absorbent article with an absorbent core 100 with multiple channels 140, 150, 160, 170, according to the prior art. The upper side of the absorbent article generally has a topsheet 300 that can be liquid pervious (not shown in FIG. 2A for clarity reasons). The lower side has a backsheet 200 (not shown in FIG. 2A for clarity reasons) that can generally be liquid impervious and is joined with the topsheet 300 at the edges of the absorbent article (not shown). In some embodiments of adult incontinence products, the topsheet 300 and the backsheet 200 are not joined at the edges. An absorbent core 100 is positioned between the topsheet 300 and the backsheet 200. The absorbent core 100 comprises absorbent material 130 arranged between a bottom core wrap sheet 120 and a top core wrap sheet 110, in such a manner that one or more channels 140, 150, 160, 170 are formed, wherein less absorbent material 130 per surface area is present in the one or more channels 140, 150, 160, 170 compared to an area around the one or more channels. An acquisition and distribution layer (ADL) 600 is provided at the top of the absorbent core 100, beneath the topsheet 300. The topsheet 300, the backsheet 200, and the absorbent core 100 can be assembled in a variety of well-known configurations. For example, the topsheet 300 and the backsheet 200 can be joined to each other by adhesive, by heat bonding, pressure bonding, ultrasonic bonding, dynamic mechanical bonding, a crimp seal, or by any other suitable securing method. In prior art embodiment the ADL 600 is typically a relatively thick layer (basis weight above 50 g/m$^2$) and comprises a coarse fibre. Further, a liquid-impermeable, either hydrophilic or hydrophobic, distribution or wicking layer 700 is included between the absorbent core 100 and the backsheet 200. This distribution or wicking layer 700 helps to wick and transport liquids and having a capability to disperse the liquid over the surface of said wicking layer from the less absorbent area's (e.g. saturated) to the more absorbent area's (e.g. unsaturated). Due to the specific absorbent capacity of the distribution or wicking layer 700, the liquid in the one or more channels will be drawn up into the distribution layer and will spread out throughout the rest of the distribution layer. In that way, the distribution, transport and absorption of the liquid can be improved.

FIGS. 1B and 2B illustrate schematically a first exemplary embodiment of the invention. The absorbent article comprises a liquid pervious topsheet 300, a liquid impervious backsheet 200, an absorbent core 100 comprising absorbent material 130, and a capillary acceleration sheet 400 between the absorbent core 100 and the liquid pervious topsheet 300. The absorbent core 100 is positioned between the liquid pervious topsheet 300 and the liquid impervious backsheet 200. The absorbent material 130 is arranged between a bottom distribution assembly 800 and a top core wrap sheet 110, such that one or more channels 140, 150, 160, 170 are formed, wherein less absorbent material 130 per surface area is present in the one or more channels 140, 150, 160, 170 compared to an area around the one or more channels, wherein preferably substantially no absorbent material is present in the one or more channels 140, 150, 160, 170. The top core wrap sheet 110 and the bottom distribution assembly 800 may be formed as one integral sheet comprising a first layer and second layer as described above in the summary.

The capillary acceleration sheet 400 may have a basis weight between 5 and 55 g/m$^2$, preferably between 8 and 50 g/m$^2$, more preferably between 10 and 20 g/m$^2$. The capillary acceleration sheet 400 may have any one or more of the features disclosed above in the summary.

The top core wrap sheet 110 is attached to the bottom distribution assembly 800 at least in a portion of the one or more channels 140, 150, 160, 170, and preferably the capillary acceleration sheet 400 is attached to the top core wrap sheet 110 in at least a portion of the one or more channels 140, 150, 160, 170. This is not shown in FIG. 1B but the skilled person understands that the capillary acceleration sheet 400 may be attached to the top core wrap sheet 110 at the level of the channels 160 and/or 170 and/or 140 and/or 150.

The capillary acceleration sheet 400 may take on any suitable shape. For example, the capillary acceleration sheet 400 may follow more or less the contours of the absorbent core 100. In other forms, the capillary acceleration sheet may comprise a rectangular shape regardless of the shape of the absorbent core 100. In some forms, the capillary acceleration sheet may be longer in length than the absorbent core 100 or shorter than the absorbent core 100. In other forms, the capillary acceleration sheet 400 may be positioned in a specific location on the absorbent core 100.

To provide for softness next to the body, the topsheet 300 can be formed from a soft, smooth, flexible, porous material that is non-irritating to the user's skin. The topsheet 300 is permeable to the body fluids to be collected by the absorbent article. Generally, topsheets for absorbent articles can be made from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibres (e.g., wood or cotton fibres), synthetic fibres (e.g., polymeric fibres such as polyester, polypropylene, or polyethylene fibres) or from a combination of natural and synthetic fibres.

Hydrophobic topsheets or topsheets with a low hydrophilicity have a reduced tendency to allow fluids to pass back through and rewet the wearer's skin. Thus, the surface of the topsheet that is in contact with the body remains dry, thereby reducing body soiling and creating a more comfortable feel for the wearer.

Example topsheets are topsheets selected from typical nonwoven forming approaches such as spunbonded, through-air bonded (TAB), carded, hydro-entangled, needled, or high loft nonwoven topsheets, and apertured 2-dimensional or 3-dimensional film topsheets. Spunbonded or through-air bonded (TAB) webs or through-air bonded carded (TABC) webs are preferred. Preferably, the through air bonded carded web comprises polyethylene/polypropylene bi-component staple fibres. "Bonded carded web" refers to webs that are made from staple fibres that are sent through a combing or carding unit, which breaks apart and aligns the staple fibres in the machine direction to form a generally machine direction-oriented fibrous nonwoven web. This web may then be drawn through a heated drum, creating bonds throughout the fabric without applying specific pressure (through air bonding process). The "Through air bonded carded web", TABCW material provides a relatively low density, lofty web.

Preferably, the topsheet has a basis weight between 10 and 30 g/m$^2$, preferably between 15 and 25 g/m$^2$. Preferably, the fibres of the topsheet have an average fineness between 1-3 dtex.

Lofty apertured formed film topsheets, with appreciable topsheet texture (nubs, micro-texture or with filament-like protrusions on the body-facing surface that can trap bodily discharges and hinder low fluid flows towards the body) that may be hydrophobic or hydrophilic in nature, can also be used.

Preferably, the capillary acceleration sheet 400 comprises a fraction of fibres having an average diameter which is at least 10% lower than an average diameter of the fibres of the liquid pervious topsheet 300, preferably at least 20% lower than an average diameter of fibres of the liquid pervious topsheet. By having a fraction of finer fibres in the capillary acceleration sheet 400 than in the topsheet 300, the liquid will pass fast through the topsheet 300 and the main capillary suction will take place in the capillary acceleration sheet. This fraction may be e.g. between 10 weight % and 50 weight % of the total amount of fibres included in the capillary acceleration sheet 400.

The capillary acceleration sheet 400 may have any one or more of the features disclosed above in the summary. Preferably, the capillary acceleration sheet is a SM nonwoven, and SMS nonwoven, a spunbond nonwoven, a carded nonwoven, a spunlace nonwoven. Preferably, the capillary acceleration sheet 400 is a spunbond meltblown nonwoven, or a spunbond meltblown spunbond nonwoven. The capillary acceleration sheet may also be a calandered spunbond nonwoven. The bonding area may be between 10 and 30%.

The capillary acceleration sheet 400 may comprise a blend of first fibres having a first average diameter and second fibres having a second average diameter. Preferably, the first average diameter is above 20 micron, more preferably above 22 micron, even more preferably above 24 micron. Preferably, the second average diameter is below 20 micron, more preferably below 19 micron, even more preferably below 18 micron. Preferably, the first fibres represent less than 50 weight % of the total amount of fibres of the capillary acceleration sheet, more preferably less than 45 weight %, and the second fibres represent more than 50 weight % of the total amount of fibres of the capillary acceleration sheet, more preferably more than 55 weight %.

Preferably, the capillary acceleration sheet 400 comprises polypropylene fibres, e.g. continuous polypropylene fibres. However, it is also possible to use other single component or bi-component fibres, such as polyethylene (PE) fibres, polyethylene-terephthalate (PET) fibres, PE/PP bi-component fibres, PE/PLA bi-component fibres. The fibres may be continuously crimped fibres. The capillary acceleration sheet may comprise fibres having substantially the same diameter or fibres having different diameters.

A further capillary acceleration sheet (not shown) may be used in addition to the capillary acceleration sheet 400 described above. However, preferably only one capillary acceleration sheet 400 is provided between the topsheet 300 and the absorbent core 100.

It is possible and advantageous to bond the topsheet 300 directly or indirectly to the underlying capillary acceleration sheet 400. These layers may be bonded by any known bonding means, such as slot gluing, spiral gluing, fusion point bonding, sealing according to a sealing pattern, or otherwise attached.

Optionally, a distribution layer may be present between the absorbent core 100 and the capillary acceleration sheet 400. However, preferably no distribution layer is present between the capillary acceleration sheet 400 and the absorbent core 100. The function of a distribution layer is to spread the insulting fluid liquid over a larger surface within the article so that the absorbent capacity of the absorbent core 100 can be more efficiently used. Typically the distribution layer is made of a nonwoven material based on synthetic or cellulosic fibres and having a relatively low density.

The capillary acceleration sheet 400 is positioned at the body-facing side of the absorbent core 100, between the topsheet 300 and the absorbent core 100 of the absorbent article, and preferably in close proximity or even in good contact with the body-facing side of the absorbent core 100. The use of a capillary acceleration sheet 400 in combination with the one or more channels 140, 150 in the absorbent core 100 leads to a very good distribution of fluids from a discharge area to the entire absorbent core 100 and an increased dryness feeling at the level of topsheet 300, and this shortly after liquid insult.

FIGS. 1C and 2C illustrate a preferred embodiment of the invention. The same or similar sheets are indicated with the same reference numeral as in FIGS. 1C and 2C and their properties may be the same as specified above unless specified otherwise below. In this embodiment, the capillary acceleration sheet 400 is attached to the bottom distribution assembly 800 at least in a portion of the one or more channels 140, 150, 160, 170. The capillary acceleration sheet 400 may have the features of any one of the embodiments disclosed in the summary.

Figures 1D, 1E:
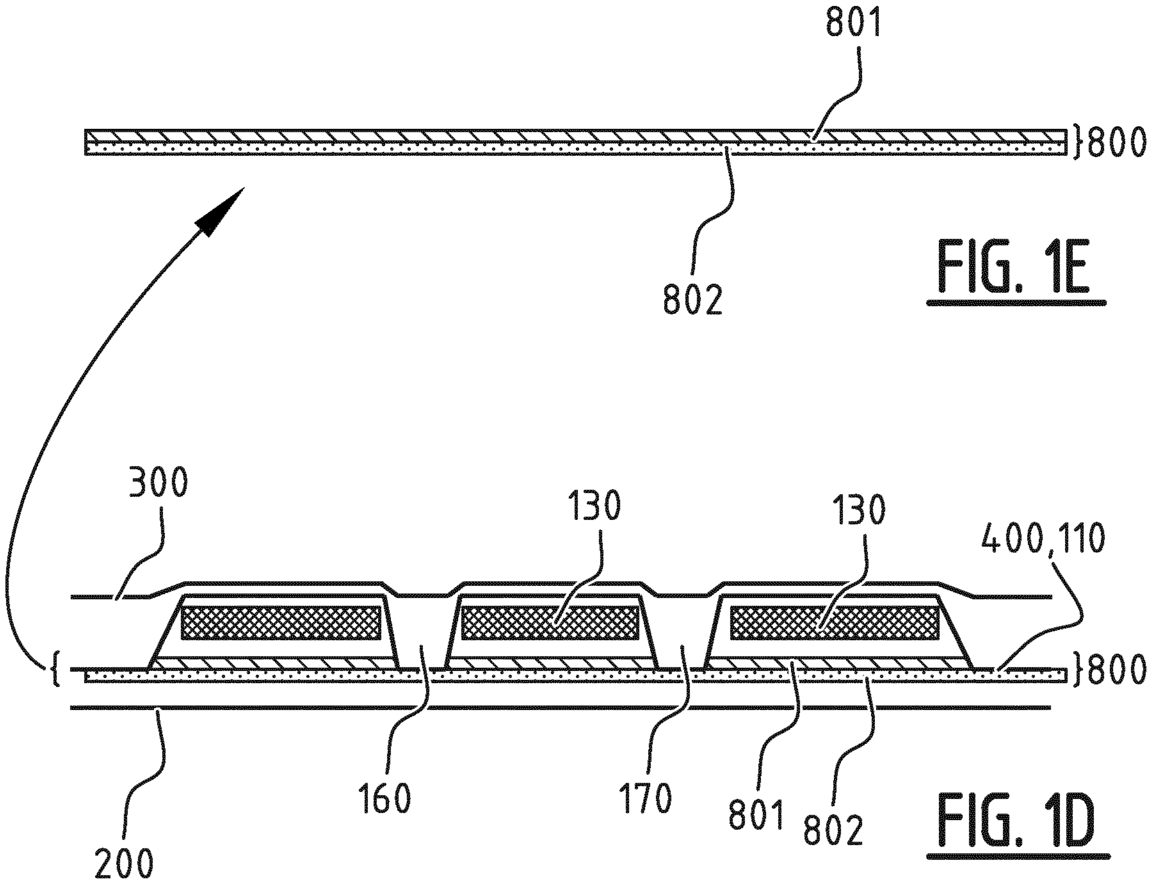
FIG. 1E is a detailed view of the bottom distribution assembly of FIG. 1D.

FIG. 1E illustrates in more detail a possible bottom distribution assembly 800 comprising a first layer 801 and a second layer 802, wherein said first layer has a first density between 20 and 150 kg/m3 and said second layer has a second density between 100 and 400 kg/m3, said second density being higher than the first density. As shown in the embodiment of FIG. 1D, the first layer 801 is closer to the absorbent material 130 than said second layer 802 which faces the backsheet 200. The absorbent article of FIG. 1D may comprise a capillary acceleration sheet 400 and/or a top core wrap sheet 110. As shown the capillary acceleration sheet 400 and/or the top core wrap sheet 110 may be attached through the first layer 801 to the second layer 802 of the bottom distribution assembly 800 in the channel areas 160, 170. Optionally also the topsheet 300 and/or the backsheet 200 may be attached at least in a portion of the channel areas 160, 170 to the bottom distribution assembly 800 (not shown). Further, the bottom distribution assembly 800 is attached along a periphery to the bottom core wrap sheet 110 and/or the capillary acceleration sheet 400. The bottom distribution assembly may be glued and/or sealed to the top core wrap sheet 110 and/or the capillary acceleration 400 at least in a portion of the one or more channels.

The bottom distribution assembly 800 may consist of a single sheet. Preferably, the bottom distribution assembly 800 is in direct contact with the superabsorbent particles of the absorbent material 130. Preferably, a difference between the first and the second density is higher than 20 kg/m3, preferably higher than 30 kg/m3 more preferably higher than 40 kg/m2, even more preferably between 50 and 150 kg/m3, most preferably between 60 and 140 kg/m3. Preferable, the second density is selected such that it forms a barrier for the superabsorbent particles.

For example, the first layer 801 may be a spunbond layer and the second layer 802 may be a spunbond layer. Preferably, the bottom distribution assembly 800 is a through-air bonded non-woven. In another example, the first layer 801 is a through-air-bonded carded non-woven and the second layer 802 is a spunbond layer.

The first layer 801 has a first basis weight and the second layer 802 has a second basis weight, said second basis weight being lower than said first basis weight. The difference between the first layer and the second layer may be larger than 1 g/m2, preferably larger than 2 g/m2, more preferably larger than 5 g/m2. The first layer may have a first basis weight between 15 and 80 g/m2, preferably between 25 and 80 g/m2, and/or the second layer may have a second basis weight between 8 and 35 g/m2, preferably between 8 and 25 g/m2. Preferably, the first layer and/or the second layer comprise more than 90 weight % of synthetic fibres, preferably more than 95 weight % of synthetic fibres.

In an example, the first layer comprises polyester fibres, and the second layer comprises any one of the following fibres or a combination thereof: polyethylene, polyester, copolyester, polypropylene, polyactic acid (PLA).

The attachment between the capillary acceleration sheet 400 and the bottom distribution assembly 800 may be a continuous or discontinuous attachment. For example, the capillary acceleration sheet 400 may be attached to the bottom distribution assembly 800 along a major portion of the one or more channels 140, 150, 160, 170, with optionally one or more unattached portions being present between attached portions. More generally, the one or more channels 140, 150, 160, 170 may comprise one or more permanent attachment portions which remain attached after wetting and/or one or more semi-permanent attachment portions which detach after wetting and/or one or more unattached portions. An unattached portion or a semi-permanent attachment portion allows for an increased swelling of the absorbent material 130 after the one or more channels 140, 150, 160, 170 have fulfilled their function of distributing the liquid. Indeed, wet absorbent material 130 is allowed to extend/swell into a portion of the channel area 140, 150, 160, 170 in case of an unattached or detached portion. No additional sheet is present between the absorbent material 130 and the capillary acceleration sheet 400. In such an embodiment, the absorbent core can thus be formed by the bottom distribution assembly 800, the capillary acceleration sheet 400, and the absorbent material 130 included between the capillary acceleration sheet 400 and the bottom distribution assembly 800. Preferably, the capillary acceleration sheet 400 extends over the full surface area of the absorbent material 130 as shown in FIGS. 1C and 2C. The capillary acceleration sheet 400 may be attached along a periphery to the bottom distribution assembly 800 in order to wrap the absorbent material 130. Thus the capillary acceleration sheet 400 may fulfil the role of top core wrap sheet whilst at the same time providing a capillary structure configured for ensuring a fast dryness of the topsheet 300. Preferably, as shown in FIGS. 1C and 2C, no additional sheet is present between the topsheet 300 and the capillary acceleration sheet 400. Thus, the capillary acceleration sheet 400 can also fulfil the role of acquiring and distributing the liquid, and does this by fast capillary suction, so that an ADL is not required between the topsheet 300 and the capillary acceleration sheet 400.

In the embodiment of FIGS. 1B and 2B and 1C and 2C, the capillary acceleration sheet 400 covers entirely the one or more channels 140, 150, 160, 170. Such an arrangement leads to a substantial improvement in the distribution of fluids over the complete absorbent core 100. Nevertheless, other arrangements also provide a good distribution of liquids. For example, the capillary acceleration sheet 400 may only partially overlap with the one or more channels 140, 150, 160, 170 or may be located between two longitudinal channels or between two lateral channels. For example, the one or more channels may extend in a front portion of the absorbent core 100 beyond a front edge of the capillary acceleration sheet 400 and/or in a rear portion of the absorbent core 100, beyond a rear edge of the capillary acceleration sheet 400. Because the capillary acceleration sheet 400 does not cover a front and/or rear end of the one or more channels, fluid in-flow and/or fluid out-flow may be increased.

Now a series of variants will be illustrated with reference to FIGS. 3-10.

FIG. 3 illustrates an exemplary embodiment of an absorbent article with an absorbent core 100 with a single central channel 180 extending in a longitudinal direction of the absorbent core 100. In FIG. 3 the capillary acceleration sheet 400 is shown to extend over only a portion of the surface area of the absorbent core 100, but it will be understood that it can also extend over the entire surface area of the absorbent core 100, similar to the embodiment of FIGS. 1C and 2C. Further, the capillary acceleration sheet 400 may be either combined with a top core wrap sheet as in the embodiment of FIGS. 1B and 2B or may replace the top core wrap sheet as in the embodiment of FIGS. 1C and 2C.

Preferably, the channel 180 extends over at least 20% of the length of the absorbent core 100, more preferably at least 30%, even more preferably at least 40%. Preferably, the channel 180 extends, seen in the transverse direction of the absorbent core, over the transverse distance which is at least 1 mm, preferably at least 3 mm, more preferably at least 4 mm, even more preferably at least 5 mm, most preferably at least 6 mm. The length 180 of the channel may be larger than 30 mm, preferably larger than 40 mm, more preferably larger than 50 mm. In the channel 180 the capillary acceleration sheet 400 may be attached to the bottom distribution assembly 800 through one or more permanent or semi-permanent attachment portions. The semi-permanent portions may be configured to release after having been in contact with liquid whilst said permanent portions may be configured not to release after having been in contact with liquid. It is noted that different types of semi-permanent attachment portions may be used in the same absorbent article so as to achieve a gradual loosening of the attachments upon wetting. The absorbent material in the absorbent core 100 preferably comprises cellulosic fluff pulp and/or superabsorbent particles. However, the absorbent material may be substantially fluffless. It is noted that it is also possible to have an embodiment with both a bottom core wrap sheet 120 and a bottom distribution assembly 800. In that case the bottom distribution assembly 800 may not be attached to the top core wrap sheet 110 and/or the capillary acceleration sheet 400, and the bottom distribution assembly 800 could be smaller and extend over only a portion of the surface area of the absorbent core 100.

Preferably, substantially no absorbent material is present in the channel 180. A position and/or shape of the channel 180 may be indicated by means of a distinguishable colour and/or coloured pattern. E.g., a position and/or shape of the channel 180 may be indicated by means of a printed ink layer. The distinguishable colour and/or coloured pattern may be provided on at least one of the topsheet, the top core wrap sheet (if present), the capillary acceleration sheet 400, the backsheet and the bottom distribution assembly.

According to a preferred embodiment, outside of the channel 180 the absorbent core has a maximum thickness and the channel 180 extends through at least 90% of the maximum thickness of the absorbent core, more preferably through substantially 100% of the thickness of the absorbent core 100 such that in the first and second attachment zone substantially no absorbent material is present between the capillary acceleration sheet 400 and the bottom distribution assembly.

According to a preferred embodiment, the attachment between the capillary acceleration sheet 400 and the bottom distribution assembly is any one of the following or a combination thereof: pressure bonding, thermal bonding, sonic bonding, chemical bonding, adhesive. The attachment may be a direct or indirect attachment. E.g. an adhesive and/or other intermediate material may be inserted between the capillary acceleration sheet 400 and the bottom distribution assembly.

FIG. 4 and FIG. 5 illustrate exemplary embodiments with two channels 140, 150. In FIGS. 4 and 5 the capillary acceleration sheet 400 is shown to extend over only a portion of the surface area of the absorbent core 100, but it will be understood that it can also extend over the entire surface area of the absorbent core 100, similar to the embodiment of FIGS. 1C and 2C. Further, the capillary acceleration sheet 400 may be either combined with a top core wrap sheet as in the embodiment of FIGS. 1B and 2B or may replace the top core wrap sheet as in the embodiment of FIGS. 1C and 2C.

The absorbent core 100 has a first and second longitudinal edge and a first and second transverse edge and the channels comprise 140, 150 are elongate channels extending from a crotch region in the direction of the first and second transverse edge. The channels 140, 150 may comprise one or more attachment zones where the capillary acceleration sheet 400 and/or the top core wrap sheet (if present), is attached to the back core wrap sheet. Preferably the one or more attachment zones are formed by any one of the following or a combination thereof: pressure bonding, thermal bonding, sonic bonding, chemical bonding, adhesive. Preferably, a width of the channels 140, 150, seen in a transverse direction of the absorbent core 100, is at least 1 mm, preferably at least 2 mm, more preferably at least 3 mm, most preferably at least 4 mm. The channels 140, 150 may comprise any one or more of the following: one or more permanent attachment zones, one or more semi-permanent attachment zones configured to release after having been in contact with liquid, one or more unattached zones.

The channels 140, 150 extend next to each other and are each extending in the direction of a first and/or second transverse edge. Preferably, the capillary acceleration sheet 400 at least partially covers both channels 140, 150. In FIG. 4 the capillary acceleration sheet 400 partially covers the channels 140, 150, whilst in FIG. 5 the channels are fully covered. Preferably, the distance between the channels 140, 150 is between 10 mm and 50 mm, preferably between 15 mm and 30 mm; and the length of the first and the second channel is larger than 60 mm, preferably larger than 70 mm.

The absorbent core 100 has a front portion extending at one side of a transverse crotch line and a rear portion extending at the other side of the transverse crotch line. In FIGS. 3-10, the front portion corresponds with an upper portion of the absorbent core 100, whilst in FIGS. 11 and 12 the front portion 100*a* corresponds with the lower portion of the absorbent core 100.

In FIGS. 4 and 5, the illustrated channels 140, 150 are straight channels but it will be understood that the channels may also be curved channels, wherein the distance between the channels increases toward the front transverse edge and/or towards the rear transverse edge of the absorbent core 100.

Figure 11:
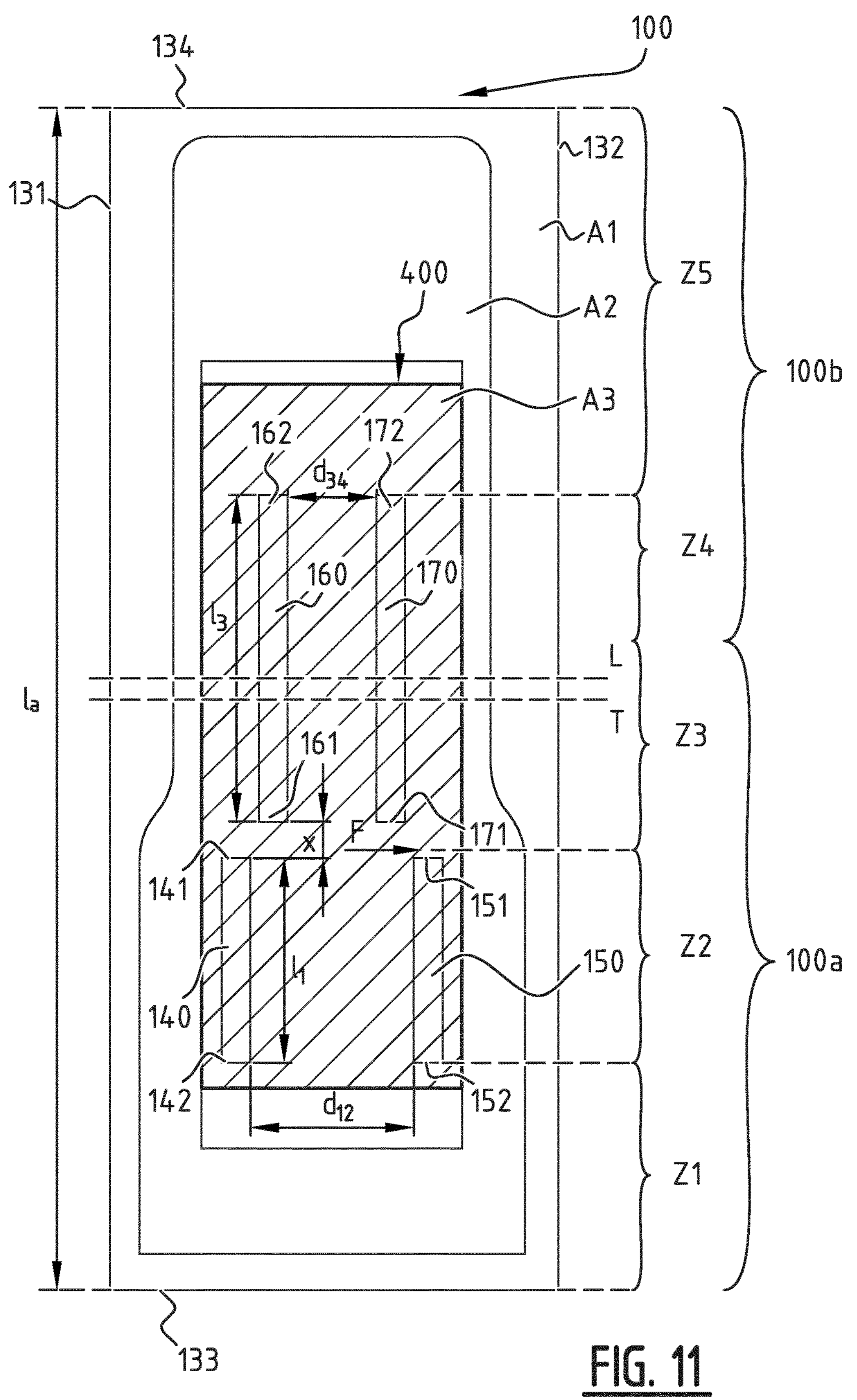
FIG. 11 is a schematic top plan view of another exemplary embodiment of a diaper with four channels.
Figure 12:
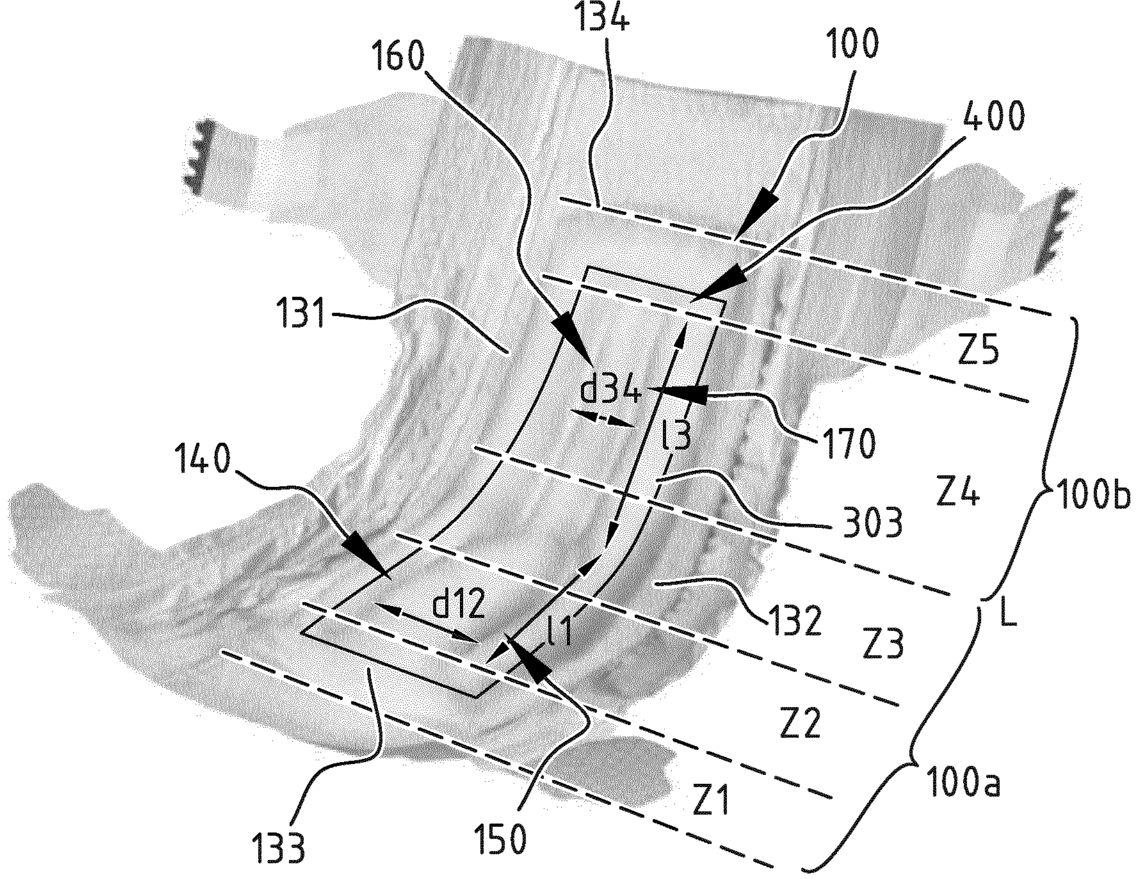
FIG. 12 is a perspective view of an exemplary embodiment of a diaper in the wetted state.

FIG. 6, FIG. 11 and FIG. 12 illustrate an embodiment with four channels: a first channel 140, a second channel 150, a third channel 160, and a fourth channel 170. In FIGS. 6, 11 and 12, the capillary acceleration sheet 400 is shown to extend over only a portion of the surface area of the absorbent core 100, but it will be understood that it can also extend over the entire surface area of the absorbent core 100, similar to the embodiment of FIGS. 1C and 2C. Further, the capillary acceleration sheet 400 may be either combined with a top core wrap sheet as in the embodiment of FIGS. 1B and 2B or may replace the top core wrap sheet as in the embodiment of FIGS. 1C and 2C.

The third and fourth channel 160, 170 are located at a distance of each other and at a distance of the first and second channel 140, 150. As illustrated, the capillary acceleration sheet 400 may covers all four channels 140, 150, 160, 170. Preferably, as illustrated in FIGS. 11 and 12, the distance between the first and the second channel 140, 150 is different from the distance between the third and the fourth channel 160, 170. Preferably, the first and second channel 140, 150 extend at least in the front portion 100*a* of the absorbent core 100, and the third and fourth channel 160, 170 extend at least in the rear portion 100*b* of the absorbent core 100, wherein preferably the distance between the first and the second channel 140, 150 is bigger than the distance between the third and the fourth channel 160, 170. Optionally, the first channel is connected to the third channel through a first semi-permanent attachment zone and the second channel is connected to the fourth attachment zone through a second semi-permanent attachment zone. Preferably, the first, second, third and fourth channels are formed by permanent attachment zones.

Optionally, a position and/or shape of one or more channels 140, 150, 160, 170 is indicated by means of a distinguishable colour and/or coloured pattern, e.g. by a printed ink layer, wherein preferably the distinguishable colour and/or coloured pattern is provided on at least one of the topsheet, the capillary acceleration sheet 400, the backsheet and the bottom distribution assembly. Preferably, the channels 140, 150, 160, 170 and the capillary acceleration sheet 400 are arranged symmetrically with respect to a longitudinal centre line of the bottom distribution assembly.

A first distance between the first and the second channel may be at least 5%, preferably at least 10% bigger, even more preferably at least 20% bigger than a second distance between the third and the fourth channel. This difference may be optimized in function of the desired used. For example, for male persons the difference may be bigger.

Seen in a projection on the longitudinal direction of the absorbent core 100, the first and the second channel may extend over a length which is less than the length of the third and fourth channel. To fit better to the body the third and fourth channel which are closer to each other may be longer to extend over a longer part of the crotch region, for example the third and fourth channel may extend both in the front and the rear portion of the absorbent core 100. Preferably, the first and the second channel extend over a length which is at least 5% less, more preferably at least 10% less than the length of the third and fourth channel. Preferably the first and the second channel extend over a length which is at least 25%, more preferably at least 35%, even more preferably at least 45% of the length of the third and fourth channel.

FIGS. 7 and 8 illustrate an absorbent article comprising an absorbent core 100 having a first and second longitudinal edge and a front and rear transverse edge. The absorbent core is provided with two interconnected elongate channels 140, 150 extending next to each other from a crotch region in the direction of the front and/or rear transverse edge and at least one connecting channel 1045, 1045' connecting the first channel with the second channel. By providing a first and a second elongate channel which are interconnected by at least one connecting channel, upon wetting of the absorbent core, liquid can flow from the first elongate channel to the second elongate channel and vice versa, improving the liquid distribution, whereupon the liquid can be absorbed by the absorbent material. In FIGS. 7 and 8, the capillary acceleration sheet 400 is shown to extend over only a portion of the surface area of the absorbent core 100, but it will be understood that it can also extend over the entire surface area of the absorbent core 100, similar to the embodiment of FIGS. 1C and 2C. Further, the capillary acceleration sheet 400 may be either combined with a top core wrap sheet as in the embodiment of FIGS. 1B and 2B or may replace the top core wrap sheet as in the embodiment of FIGS. 1C and 2C.

In FIG. 7 the at least one connecting channel comprises a rear connecting channel 1045 which connects a rear end portion of the first channel 140 to a corresponding rear end portion of the second channel 150. In FIG. 8 both a rear connecting channel 1045 and a front connecting channel 1045' which connects a front end portion of the first channel to a corresponding front end portion of the second channel, are provided. In that manner a good distribution is obtained in the front portion and/or in the rear portion. Especially for a male person, it may be desirable to have a front connecting channel.

The absorbent core 100 has a transverse crotch line dividing the absorbent core in a front portion and a rear portion on either side of the transverse crotch line. Preferably, the front connecting channel is located in the front portion and/or the rear connecting channel is located in the rear portion.

Preferably, the absorbent core 100 is substantially symmetrical with respect to a longitudinal center axis. For example, the channel area 140, 150, 1045, 1045' may be substantially V-shaped or U-shaped or O-shaped, wherein the V-shape or U-shape is arranged such that it is symmetrical with respect to the longitudinal center axis of the absorbent core.

In an exemplary embodiment, the first and second channels are permanent attachment zones which remain attached upon wetting, or semi-permanent attachment zones configured to release after having been in contact with liquid for a predetermined period of time, wherein said predetermined period of time is preferably smaller than 30 s. In a preferred embodiment the at least one connecting channel 1045, 1045' comprises any one or more of: a permanent attachment portion which remains attached upon wetting, a semi-permanent attachment portion configured to release after having been in contact with liquid for a predetermined period of time, wherein said predetermined period of time is preferably smaller than 30 s, and unattached portion. Attachment portion/zone refers to a portion/zone where the capillary acceleration sheet 400 (and if present also the top core wrap sheet) is attached to the bottom distribution assembly.

In an exemplary embodiment, the first channel and the second channel are substantially parallel and extend in a longitudinal direction of the absorbent core 100. In another embodiment, see FIG. 7, the first and second channel 140, 150 may diverge in the direction of the front edge of the absorbent core 100.

In an exemplary embodiment, the largest distance between the first and the second channel in the transverse direction is between 15 and 70% of the width of the absorbent core, more preferably between 20 and 50%; wherein preferably the largest distance between the first and the second attachment zone in the transverse direction is between 10 mm and 100 mm, more preferably between 20 mm and 80 mm, even more preferably between 30 mm and 70 mm.

FIG. 9 illustrates an embodiment with an X-shaped channel area. In FIG. 9, the capillary acceleration sheet 400 is shown to extend over only a portion of the surface area of the absorbent core 100, but it will be understood that it can also extend over the entire surface area of the absorbent core 100, similar to the embodiment of FIGS. 1C and 2C. Further, the capillary acceleration sheet 400 may be either combined with a top core wrap sheet as in the embodiment of FIGS. 1B and 2B or may replace the top core wrap sheet as in the embodiment of FIGS. 1C and 2C.

The absorbent core 100 has a first and second longitudinal edge and a first and second transverse edge, and a longitudinal center line dividing the absorbent core in a first longitudinal portion and a second longitudinal portion on either side of the longitudinal center line, and a transverse crotch line dividing the absorbent core in a front portion and a rear portion on either side of the transverse crotch line. The absorbent core is provided with a plurality of channels 140, 150, 160, 170 comprising a first channel 140, 170 and second channel 150, 160 extending next to each other from a crotch region in the direction of the front and rear transverse edge. The first channel 140, 170 crosses the longitudinal center line in a first crossing point, from the first longitudinal portion to the second longitudinal portion; and the second elongate channel 150, 160 crosses the longitudinal center line in second crossing point, from the second longitudinal portion to the first longitudinal portion. The first and second crossing point may be the same point (as in FIG. 9) or a different point, and may be located in the front portion or in the rear portion or on the transverse crotch line between connecting the front portion to the rear portion. By providing a first and a second channel which are crossing the longitudinal center line, upon wetting of the absorbent core 100, liquid is guided in the first and/or second elongate channel from left to right and/or from right to left, respectively, whilst flowing towards the crotch region or away from the crotch region, improving the liquid distribution, whereupon the liquid can be absorbed by the absorbent material. Further, by making the first and second channels cross the longitudinal center line, the channels may be longer compared to similar channels extending parallel to the longitudinal center line, resulting in a larger liquid distribution zone.

Preferably, the first and/or second crossing point are located at a distance of the transverse crotch line. For example, the first and/or second crossing point may be located in a front portion. In that way the position of the first and/or second can be optimized e.g. in function of whether the absorbent article is intended for a male or female person. However, in other embodiments, the first and/or second crossing point may be located on the transverse crotch line. When at a distance of the transverse crotch line, preferably, the distance between the first and/or second crossing point and the transverse crotch line is larger than 1% of the length of the absorbent core, preferably larger than 2%, even more preferably larger than 3%.

In certain embodiments with multiple first crossing points and/or multiple second crossing points, these multiple first and/or second crossing points may be located a different distances of the transverse crotch line, and may comprise e.g. two first crossing points, one in the front portion and one in the rear portion, and two second crossing points, one in the front portion (optionally corresponding with the first crossing point in the front portion), and one in the rear portion (optionally corresponding with the first crossing point in the rear portion).

Preferably, the first elongate channel 140, 170 extends both in the front portion and in the rear portion; and the second elongate channel 150, 160 extends both in the front portion and in the rear portion. In that manner a good liquid distribution from left to right and from front to rear can be obtained. Preferably, the first elongate and the second elongate channels are arranged symmetrically with respect to the longitudinal center line of the absorbent core. Preferably, a maximum distance between the first and the second elongate attachment zone is between 15 and 70% of the width of the absorbent core, more preferably between 20 and 50%.

In an exemplary embodiment a maximum distance between the first and the second channel in the front portion is different from a maximum distance between the first and the second channel in the rear portion. In that manner the liquid distribution zone may be better adapted to the type of person wearing the absorbent article. For example, for a male person, a maximum distance between the distance between the first and the second attachment zone near a front transverse edge may be larger than a maximum distance between the first and the second attachment zone in a rear portion.

Preferably, the length of the first and second channel is larger than 10% of the length of the absorbent core, more preferably larger than 30%, even more preferably larger than 50%.

In an exemplary embodiment, the first and second channel together form a substantially X-shaped zone. Optionally the legs of the "X" may be interrupted to create one or more bridging zones.

FIG. 10 illustrates an embodiment of an absorbent article with an absorbent core 100 comprising three channels 140, 150, 180. In FIG. 10, the capillary acceleration sheet 400 is shown to extend over only a portion of the surface area of the absorbent core 100, but it will be understood that it can also extend over the entire surface area of the absorbent core 100, similar to the embodiment of FIGS. 1C and 2C. Further, the capillary acceleration sheet 400 may be either combined with a top core wrap sheet as in the embodiment of FIGS. 1B and 2B or may replace the top core wrap sheet as in the embodiment of FIGS. 1C and 2C.

The channels comprise a first and second channel 140, 150 similar to the first and second channel of FIG. 6, and a third channel 180 extending from the crotch region in the direction of the second transverse edge, wherein seen in a projection on a transverse direction the third channel 180 is located between the first and the second channel 140, 150. By having a first and a second channel in the front or rear portion and a third channel in the rear or front portion, respectively, it is possible to tailor the absorbent article to the wearer. For example, for a male person the first and second channel may be in the front portion and the third channel may be in the rear portion, whilst for a female person the first and second channel may be in the rear portion and the third channel in the front portion. Further it is possible to optimize the difference between the front and the rear portion for obtaining a unisex absorbent article.

Seen in a projection on the longitudinal direction of the absorbent core, the first and the second channel 140, 150 may extend over a length which is less than the length of the third channel 180. To fit better to the body the third channel 180 may be longer to extend over a longer part of the crotch region, for example the third channel may extend both in the front and the rear portion of the absorbent core. Preferably, the first and the second channel extend over a length which is at least 5% less, more preferably at least 10% less than the length of the third channel. Preferably the first and the second channel extend over a length which is at least 25%, more preferably at least 35%, even more preferably at least 45% of the length of the third channel.

For all embodiments described above, preferably, the one or more channels cover together at least 20%, preferably at least 30%, more preferably at least 40%, more preferably at least 50%, more preferably at least 60%, more preferably at least 70%, more preferably 80% and more preferably at least 90% of a total length of the absorbent core. The covered length may be realized with a single channel or with a combination of two or more channels. This will allow a good distribution over the entire absorbent core as well as a good formation of the channels/embankments and will give the absorbent article a tub-shape upon swelling of the absorbent core.

The absorbent article 100 may further comprise a wetness indicator preferably placed between two channels and/or in one or more channels and/or between a channel and an edge of the absorbent core. The wetness indicator may change appearance when contacted with liquid, e.g. the wetness indicator may be configured to generate a colour change signal that changes appearance when contacted with liquid. The wetness indicator may comprise a composition that changes appearance when contacted with liquid, in particular a composition comprising a pH indicator and/or a water soluble dye. The composition may comprise a stabilizer, a colorant, and a matrix.

Figure 13:
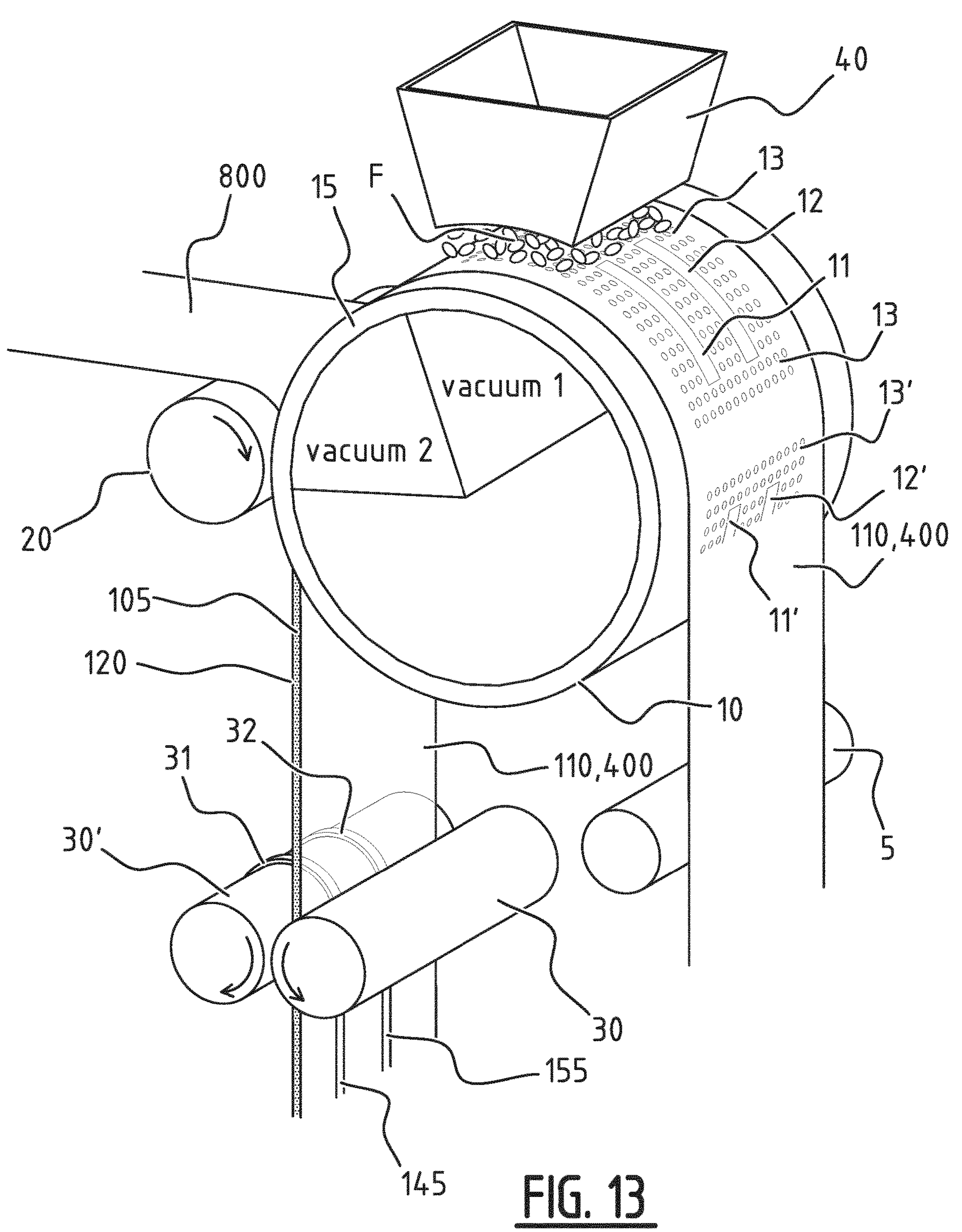
FIG. 13 illustrates schematically an exemplary embodiment of a method and apparatus for manufacturing an absorbent article.

FIG. 13 illustrates an embodiment of a method for manufacturing an absorbent article. The method comprises in a first step guiding a first sheet material 110, 400 along an optional guide roller 5, and further along a rotating member 10, wherein a surface 15 of said rotating member 10 is provided with a pattern with suction zones 13, 13' and non-suction zones 11, 12; 11', 12'. The first sheet material 110, 400 is shown in a transparent manner to reveal the suction and non-suction zones of the rotating member 10. The suction zones 13, 13' may be provided with holes, and the non-suction zones 11, 12; 11', 12' are formed of closed material. For example, the non-suction zones 11, 12; 11', 12' may be provided with inserts. The inserts 11, 12; 11', 12', may have a trapezoidal cross section. FIG. 10 shows an insert pattern with four non-suction zones per absorbent core, but it will be understood that the number of inserts depends on the number of channels to be realized. The inserts may be fixed e.g. with screws on the rotating member 10. At an inner area of the rotating member 10 a vacuum is applied, see VACUUM 1. The non-suction zones 11, 12; 11', 12' comprise at least a first elongate zone 11, 11' and a second elongate zone 12, 12' extending in a circumferential direction of the rotating member 10. In a second step an absorbent material F is applied via a hopper 40 on said first sheet material 110, 400 on the rotating member 10 such that the suction zones 13, 13' are covered with absorbent material and substantially no absorbent material is present on the non-suction zones 11, 12; 11', 12'. In a third step a second sheet material 800 is applied on top of the absorbent material on the first sheet material 110, 400, e.g. using a further rotating member 20. In the illustrated embodiment, the first sheet material 110, 400 may be the capillary acceleration sheet material 400 or the top core wrap sheet material 110 or a combination thereof, and the second sheet material 800 may be bottom distribution assembly. However, in another embodiment, the second sheet material is the top core wrap sheet material or the capillary acceleration sheet material or a combination thereof, and the first sheet material may be the bottom distribution assembly. In a fourth step the first sheet material 110 is attached to the second sheet material 800 at least in the areas where substantially no absorbent material is present, and such that one or more channels 140, 150, 160, 170 are formed. The attaching may be done by applying pressure and/or heat and/or ultrasonic energy on the sandwich formed by the first sheet material 110, 400 and on the second sheet material 800, especially in the one or more channels where substantially no absorbent material is present, e.g. by a rotating member 30 and/or opposite rotating member 30' which is provided with at least a first and a second seal rib 31, 32 dimensioned for applying pressure and heat in the areas where substantially no absorbent material is present in order to create the channels 140, 150, 160, 170, respectively.

The capillary acceleration sheet 140 and the bottom distribution assembly 800 may have any one of the features described above or described in the summary. Also the top core wrap sheet 110, if present, may have any one of the features described above.

While the above-described method of manufacturing absorbent articles has good results, the first sheet material and the second sheet material may be additionally attached using a binder, such as glue, to strengthen the bond between the first and second sheet material. For example, gluing may be performed as described in patent EP 3 453 368 B1 in the name of the applicant, which is included herein by reference.

When a the top core wrap sheet 110 is present, the capillary acceleration sheet material 400 may also be first laminated, e.g. adhered, to a topsheet material, and the combination of the capillary acceleration sheet 400 and the topsheet may then be arranged against the top core wrap sheet 110, wherein optionally the capillary acceleration sheet 400 may be glued to the top core wrap sheet 110.

Also, when no the top core wrap sheet 110 is present, the capillary acceleration sheet material 400 may also be first laminated, e.g. adhered, to a topsheet material, and the combination of the capillary acceleration sheet 400 and the topsheet may then be the first sheet material in the method of FIG. 13.

Figures 14A, 14B, 14C, 14D, 14E:
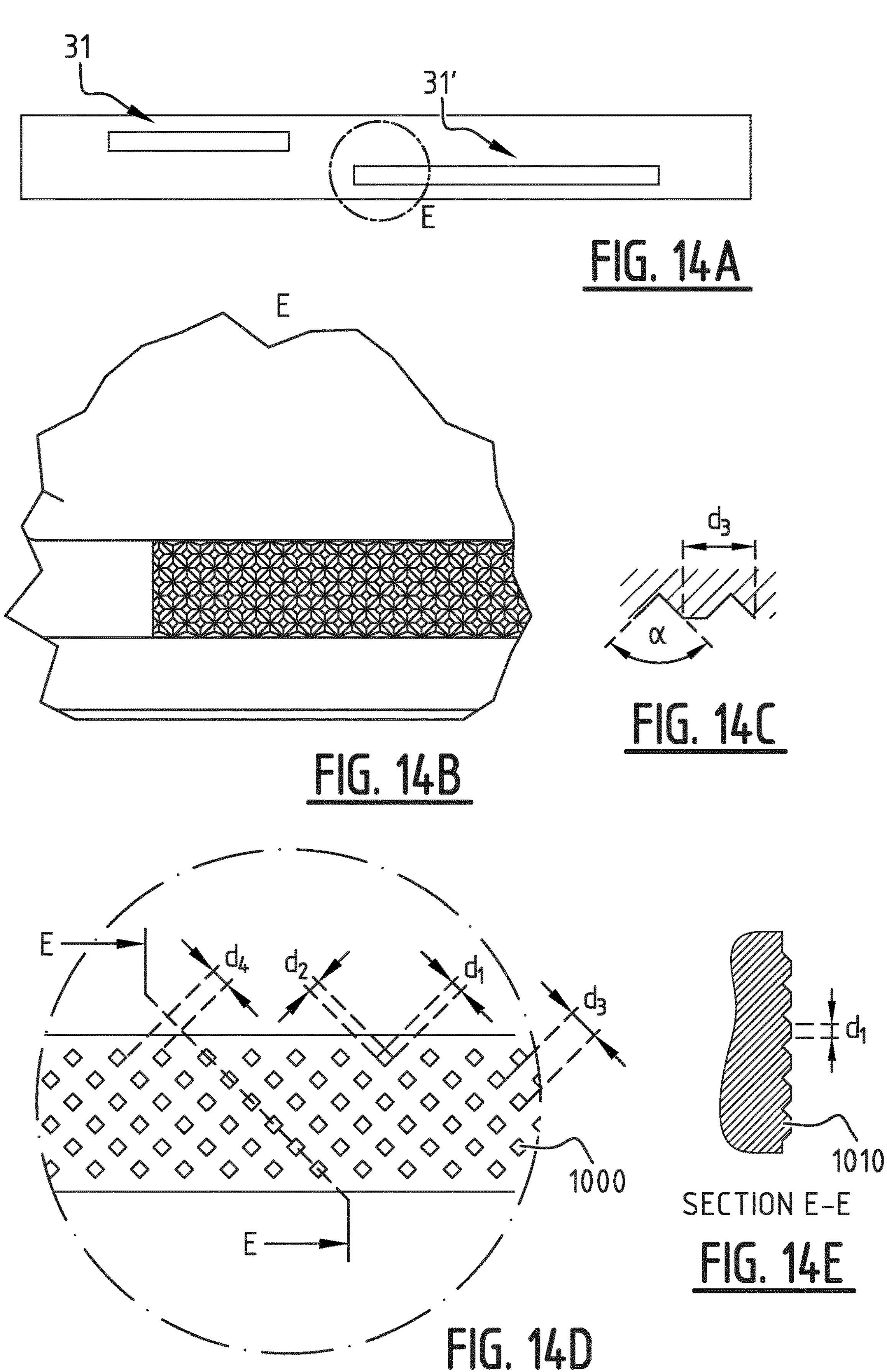
FIGS. 14A-E illustrate an example of a set of sealing bars having a sealing pattern.

FIGS. 14A-E illustrate an example of a set of sealing bars 31, 31' having a first sealing pattern. The sealing bars 31, 31' may be intended to seal e.g. channels 170 and 140. It will be understood that one or more sealing bars may be used in accordance with the one or more channels to be sealed. A detail of the sealing pattern is visible in the top view of FIG. 14B and in FIG. 14D which illustrates the areas where sealing will take place. Here the sealing pattern is a regular pattern of square shaped dots 1000. FIG. 14E shows a cross section and illustrates that the dots are achieved by protrusions 1010. Each protrusion 1010 preferably has a flat top surface forming a dot 1000 of the sealing pattern, and an inclined peripheral surface. If an absorbent particle were to be present near the flat top surface it can easily migrate in a recess delimited by the inclined peripheral wall.

Preferably, the sealing pattern (i.e. the total surface area of the dots 1000) covers less than 80%, preferably less than 70%, more preferably less than 60%, even more preferably less than 50%, most preferably between 1 and 50% of the surface area of the one or more channels. For example, the sealing pattern covers between 1 and 50% of the total surface area of the one or more channels, or between 1 and 40%, or between 1 and 30%, or between 1 and 25%, or between 2 and 25%, or between 3 and 25%, or between 4 and 25%.

Such sealing pattern can provide a good resistance against the swell forces generated by liquid being captured in the superabsorbent particles by hydrogen bonds, but the sealing pattern equally can provide resistance against dry and wet superabsorbent particles trying to penetrate through the capillary acceleration sheet and through the sealing pattern after as well as during the sealing step of the manufacturing process. In that manner, any risk of dry or wet SAP particles coming into contact with sensitive skin upon wearing is avoided or reduced. Further, by having a reduced surface area that is being sealed in accordance with a pattern, any particles remaining in the one or more channel zones can easily migrate to a non-sealing area so that the risk of creating holes in the one or more channel zones is reduced or avoided.

Although a pattern of dots 100 is illustrated, the skilled person understands that other sealing patterns are possible, such as a line pattern e.g. a grid, etc. Also, the dots may have any shape, e.g. round, polygonal, etc. The line pattern may comprise one or more sets of parallel lines. When a first set of parallel lines and a second set of parallel lines are included, the lines of the first set may be oriented at a non-zero angle with respect to the lines of the second set.

Preferably, the sealing pattern comprises a large number of distinct sealing areas (here dots 1000) spread across the one or more channels. Preferably, the large number is larger than 10, more preferably larger than 20.

Preferably, the sealing pattern comprises a plurality of discrete elements (here dots 1000), and each discrete element has a first dimension in a first direction and a second dimensions in a direction perpendicular to the first direction. The first dimension is smaller than 2 mm, preferably smaller than 1.5 mm, more preferably smaller than 1 mm, e.g. between 0.1 and 0.7 mm or between 0.2 and 0.7 mm, or between 0.3 and 0.6 mm, e.g. 0.5 mm as illustrated.

Preferably, the distance between adjacent discrete elements (here dots 1000) is smaller than 10 mm, preferably smaller than 5 mm, more preferably smaller than 2 mm, e.g. between 0.1 and 2.0 mm or between 0.2 and 1.5 mm, or between 0.3 and 1.0 mm, e.g. 0.7 mm as illustrated.

GLOSSARY

As used in the present application, the following terms have the following meanings:

"A", "an", and "the" as used herein refers to both singular and plural referents unless the context clearly dictates otherwise. By way of example, "an edge barrier" refers to one or more than one edge barrier.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or variations are appropriate to perform in the disclosed invention. However, it is to be understood that the value to which the modifier "about" refers is itself also specifically disclosed.

"Absorbent article", "absorbent garment", "absorbent product", "absorbing article", "absorbing garment", "absorbing product" and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to permanently absorb and/or retain bodily exudates.

"Absorbent component" as used herein refers to a structural constituent of an absorbent article, e.g., a piece of an absorbent core, such as one of multiple pieces in a multi-piece absorbent core.

"Absorbent element" as used herein refers to a part of a functional constituent of an absorbent structure, e.g., an acquisition layer, a dispersion layer, core layer or a release structure formed of a material or materials having particular liquid handling characteristics suitable for the specific function.

"Absorbent fibrous polymer material" as used herein refers to an absorbent polymer material which is in threadlike from such as fibers, filaments, and the like so as to be less flowable in the dry state than particulates.

"Absorbent insert" as used herein refers to a device adapted for insertion into an "Absorbent layer" as used herein refers to a term referring to a discrete, identifiable sheet-like or web-like element of an absorbent article which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g bond area's) or unintentional (e.g. manufacturing artifacts).

"Absorbent particulate polymer material" as used herein refers to an absorbent polymer material which is in particulate form such as powders, granules, flakes and the like so as to be flowable in the dry state.

"Absorption" as used herein refers to the process by which a liquid is taken up within a material.

"Absorption rate" as used herein refers to the rate of absorption of liquid, i.e. the amount of liquid which is absorbed per unit of time, typically by an absorbent component, element and/or absorbent layer of the absorbent article, structure and/or core.

"Acquisition layer", "acquisition region", "acquisition surface" or "acquisition material" and the like as used herein refer to the layer overlying the absorbent core having a faster liquid uptake and/or distribution capability.

"Absorbency" is the ability of a material to take up fluids by various means including capillary, osmotic, solvent, chemical and/or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibers or particles in an air stream and condensing them from the air stream onto a moving screen by means of a pressure and/or vacuum; a web of fibers produced by airlaying is herein referred to an "airlaid"; an airlaid web bonded by one or more techniques to provide fabric integrity is herein referred to an "airlaid nonwoven".

"Apparent density", "density" as used herein refers to the basis weight of the sample divided by the caliper with appropriate unit conversions incorporated therein. Apparent density used herein has the unit g/cm3.

"Attach", "attached" and "attachment" as used herein are synonymous with their counterparts of the terms "fasten", "affix", "secure", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, g/m2 or gsm.

"Bodily exudates", "body exudates", "bodily fluids", "body fluids", "bodily discharges", "body discharges", "fluid(s)", "liquid(s)", "fluid(s) and liquid(s) and the like as used herein are used interchangeably and refer to, but are not limited to urine, blood, vaginal discharges, breast milk, sweats and fecal matter.

"Binder", "adhesive", "glue", "resins", "plastics" and the like as used herein are used interchangeably and refer to substances, generally in a solid form (e.g. powder, film, fiber) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibers" as used herein refers to naturally occurring fibers based on cellulose, such as, for example cotton, linen, etc; wood pulp fibers are one example of cellulose fibers; man-made fibers derived from cellulose, such as regenerated cellulose (rayon), or partially or fully acetylated cellulose derivatives (e.g. cellulose acetate or triacetate) are also considered as cellulose fibers.

"Cluster" or the like as used herein refers to an agglomeration of particles and/or fibers.

"Chemically stiffened fibers", chemically modified fibers", "chemically cross-linked fibers", "curly fibers" and the like as used herein are used interchangeably and refer to any fibers which have been stiffened by chemical means to increase stiffness of the fibers under both dry and aqueous conditions, for example by way of addition of chemical stiffening agents (e.g. by coating, impregnating, etc), altering the chemical structure of the fibers themselves (e.g. by cross-linking polymer chains, etc) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or "contain", "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight non-woven material used to contain and conceal an underlying absorbent core material; examples are the facing layer or materials that cover the absorbent cores of feminine hygiene garment s, baby diapers and pants and adult incontinence garments.

"Crotch region" of an absorbent article as used herein refers to about 50% of the absorbent article's total length (i.e., in the y-dimension), where the crotch point is located in the longitudinal center of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place; the setting may occur by removing solvent or by cross-linking so as to make them in soluble.

"Diaper", "conventional diaper", "diaper-like", "diaper-like garment" and the like as used herein are used interchangeably and refer to disposable absorbent articles, which typically include a front waist portion and a back waist portion which may be releasable connected about the hips of the wearer during use by conventional fasteners such as adhesive tape fasteners or hook and loop type fasteners. In use, the article is positioned between the legs of the wearer and the fasteners are releasable attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Dispersion layer", "dispersion region", "dispersion surface" or "dispersion material" and the like as used herein refer to the layer overlying the absorbent core having a faster liquid uptake and dispersion capability.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Drylaying" as used herein refers to a process for making a nonwoven web from dry fiber; these terms apply to the formation of carded webs, as well as to the air laying formation of random webs; a web of fibers produced by drylaying is herein referred to as a "drylaid"; a drylaid web bonded by one or more techniques to provide fabric integrity is herein referred to a "drylaid nonwoven".

"Dry strength" as used herein refers to the strength of ajoint determined in dry state conditions, immediately after drying under specified conditions or after a period of conditioning in the standard laboratory atmosphere.

"Essentially cellulose free", "substantially fluffless" or "little to no cellulose fibers" as used herein refers to an absorbent article, structure, core component and/or element containing less than 20% by weight cellulosic fibers, less than 10% cellulosic fibers, less than 5% cellulosic fibers, no cellulosic fibers, or no more than an immaterial amount of cellulosic fibers which do not materially affect the thinness, flexibility or absorbency thereof.

"Essentially fluffless" or "little to no fluff pulp" as used herein refers to an absorbent article, structure, core, component and/or element containing less than 20% by weight fluff pulp, less than 10% fluff pulp, less than 5% fluff pulp, no fluff pulp, or no more than an immaterial amount of fluff pulp which do not materially affect the thinness, flexibility or absorbency thereof.

"Fabric" as used herein refers to a sheet structure made from fibers, filaments and/or yarns.

"Feminine hygiene garments" as used herein refer to absorbent hygiene articles intended to be worn by woman, for absorbing and containing body exudates.

"Fiber" as used herein refers to the basic threadlike structure from which nonwovens, yarns and textiles are made. It differs from a particle by having a length at least 4 times its width; "Natural fibers" are either of animal (wool, silk), vegetable (cotton, flax, jute) or mineral (asbestos) origin, while "Man-made fibers" may be either polymers synthesized from chemical compounds (polyester, polypropylene, nylon, acrylic etc.) or modified natural polymers (rayon, acetate) or mineral (glass). "Fiber" and "filament" are used interchangeably.

"Fluff pulp" or "Pulp fluff" as used herein refers to wood pulp specially prepared to be drylaid. The fibers can be either natural or synthetic or a combination thereof.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the backsheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"High loft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilization layer" as used herein refers to a layer able to be applied to the absorbent polymer material or absorbent polymer material area with the intent to gather, bond and/or immobilize absorbent material and/or absorbent layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibers with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered."

"Upper" refers to the layer of the absorbent article which is nearest to and/or faces the wearer facing layer; conversely, the term "lower" refers to the layer of the absorbent article which is nearest to and/or faces the garment facing layer. "Layer" is three dimensional structure with a x dimension width, y dimension length, and z-dimensions thickness or caliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the flow of a liquid from one absorbent element or component to another absorbent element or component by channel flow action.

"Mechanical bonding" as used herein refers to a method of bonding fibers by entangling them. This can be achieved by needling, stitching with fibers or by the use of high-pressure air or water jets and the like.

"Nonwoven" as used herein refers to manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as melt blowing, spun bonding, solvent spinning, electrospinning, and carding. The basis weight of nonwoven fabrics is usually expressed in grams per square meter (gsm).

"Pant", "training pant", "closed diapers", "prefastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or nonrefastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Release structure", "release region", "release surface" or "release material" and the like as used herein are used interchangeably and refer to a structure in fluid communication with the absorbent core having a larger relative liquid absorption capacity and/or rate allowing it to quickly take up, temporarily hold and releasing liquids.

"Resin" as used herein refers to a solid or semisolid polymeric material.

"Thermobonding" as used herein refers to a method of bonding fibers by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localized heat through vibration thereby causing thermoplastic fibers to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibers produced by weaving is herein referred to as a "woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (they-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or nonwoven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, nonwoven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of a joint determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibers by applying modified paper making techniques; a web of fibers produced by wetlaying is herein referred to as a "wetlaid".

"Wood pulp" as used herein refers to cellulosic fibers used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

The invention claimed is:

1. An absorbent article comprising a liquid pervious topsheet, a liquid impervious backsheet, absorbent material positioned between the liquid pervious topsheet and the liquid impervious backsheet, and a bottom distribution assembly between the absorbent material and the liquid impervious backsheet, wherein the absorbent material comprises superabsorbent particles and is arranged such that one or more channels are formed, wherein less absorbent material per surface area is present in the one or more channels compared to an area around the one or more channels, wherein the bottom distribution assembly comprises a first layer and a second layer, wherein said first layer has a first density between 20 and 150 kg/m3 and said second layer has a second density between 100 and 400 kg/m3, said second density being higher than the first density, wherein said first layer is closer to the absorbent material than said second layer;

wherein a difference between the first and the second density is higher than 20 kg/m3.

2. The absorbent article of claim 1, wherein the bottom distribution assembly consists of a single sheet.

3. The absorbent article of claim 1, wherein the bottom distribution assembly is in direct contact with the superabsorbent particles.

4. The absorbent article of claim 1, wherein a difference between the first and the second density is higher than 30 kg/m3.

5. The absorbent article of claim 1, wherein the first layer is a spunbond layer and the second layer is a spunbond layer.

6. The absorbent article of claim 1, wherein the first layer is a through-air-bonded carded non-woven and the second layer is a spunbond layer.

7. The absorbent article of claim 1, wherein the bottom distribution assembly is a through-air bonded non-woven.

8. The absorbent article of claim 1, wherein the first layer has a first basis weight and the second layer has a second basis weight, said second basis weight being lower than said first basis weight, wherein the difference between the first layer and the second layer is larger than 1 g/m2.

9. The absorbent article of claim 1, wherein the first layer has a first basis weight between 15 and 80 g/m2 and/or wherein the second layer has a second basis weight between 8 and 35 g/m2.

10. The absorbent article of claim 1, wherein the first layer and/or the second layer comprise more than 90 weight % of synthetic fibres.

11. The absorbent article of claim 1, wherein the first layer comprises polyester fibres.

12. The absorbent article of claim 1, wherein the second layer comprises any one of the following fibres or a combination thereof: polyethylene, polyester, copolyester, polypropylene, polyactic acid (PLA).

13. The absorbent article of claim 1, wherein the second density is selected such that it forms a barrier for the superabsorbent particles.

14. The absorbent article of claim 1, further comprising a top core wrap sheet and/or a capillary acceleration sheet between the absorbent material and the topsheet, wherein the bottom distribution assembly is attached to the top core wrap sheet and/or the capillary acceleration at least in a portion of the one or more channels.

15. The absorbent article of claim 14, wherein the bottom distribution assembly is glued to the top core wrap sheet and/or the capillary acceleration at least in a portion of the one or more channels.

16. The absorbent article of claim 14, wherein the bottom distribution assembly is sealed in accordance with a sealing pattern to the top core wrap sheet and/or to the capillary acceleration sheet at least in a portion of the one or more channels, wherein the sealing is realized by heat and/or pressure and/or ultrasonic energy.

17. The absorbent article of claim 16, wherein the sealing pattern is a regular pattern.

18. The absorbent article of claim 16, wherein the sealing pattern comprises a large number of distinct sealing areas spread across the one or more channels, wherein the large number is larger than 10.

19. The absorbent article of claim 16, wherein the sealing pattern comprises a plurality of discrete elements, and wherein each element has a first dimension in a first direction and a second dimensions in a direction perpendicular to the first direction, and wherein the first dimension is smaller than 2 mm.

20. The absorbent article of claim 1, wherein the bottom distribution assembly comprises a spunbond layer and a meltblown layer, wherein said spunbond layer comprises polyester fibres, wherein the spunbond layer is arranged closer to the absorbent material than the meltblown layer.

21. The absorbent article of claim 20, wherein the bottom distribution assembly is a spunbond meltblown spunbond nonwoven comprising the spunbond layer, the meltblown layer and a second spunbond layer on the other side of the meltblown layer.

22. The absorbent article of claim 21, wherein the second spunbond layer comprises polypropylene fibres.

23. The absorbent article of claim 1, further comprising a capillary acceleration sheet and/or a top core wrap sheet between the topsheet and the absorbent material, wherein the bottom distribution assembly is attached to the capillary acceleration sheet and/or the top core wrap sheet at least in a portion of the one or more channels.

24. A method for manufacturing an absorbent article, comprising the steps of providing a liquid pervious topsheet and a liquid impervious backsheet; arranging an absorbent material, between a bottom distribution assembly, on one side, and a top core wrap sheet and/or a capillary acceleration sheet, on the other side, such that one or more channels are formed, wherein less absorbent material per surface area is present in the one or more channels compared to areas around the one or more channels; and arranging the liquid pervious topsheet at the side of top core wrap sheet and/or the capillary acceleration sheet and the liquid impervious backsheet at the side of the bottom distribution assembly, wherein the absorbent article has the features defined in claim 1.

* * * * *